US010894960B2

(12) United States Patent
Ziady et al.

(10) Patent No.: US 10,894,960 B2
(45) Date of Patent: Jan. 19, 2021

(54) COMPOSITIONS AND METHODS FOR NUCLEIC ACID TRANSFER

(71) Applicant: Children's Hospital Medical Center, Cincinnati, OH (US)

(72) Inventors: Assem G. Ziady, Newport, KY (US); Matthew Siefert, Cincinnati, OH (US); Songbai Lin, Lawrenceville, GA (US); Harrison Brown, Atlanta, GA (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 15/690,526

(22) Filed: Aug. 30, 2017

(65) Prior Publication Data
US 2018/0057813 A1  Mar. 1, 2018

Related U.S. Application Data

(60) Provisional application No. 62/381,237, filed on Aug. 30, 2016.

(51) Int. Cl.
| | | |
|---|---|---|
| *C12N 15/113* | (2010.01) |
| *A61K 38/17* | (2006.01) |
| *A61K 47/60* | (2017.01) |
| *A61K 47/64* | (2017.01) |
| *A61K 31/713* | (2006.01) |
| *A61K 31/395* | (2006.01) |
| *A61K 31/4709* | (2006.01) |
| *A61K 31/565* | (2006.01) |
| *A61K 31/132* | (2006.01) |
| *A61K 31/573* | (2006.01) |
| *A61K 31/352* | (2006.01) |
| *A61K 31/265* | (2006.01) |
| *A61K 31/05* | (2006.01) |
| *A61K 31/704* | (2006.01) |
| *A61K 31/519* | (2006.01) |
| *A61K 31/52* | (2006.01) |
| *A61K 31/7048* | (2006.01) |
| *A61K 48/00* | (2006.01) |
| *A61K 31/7088* | (2006.01) |
| *C12N 15/85* | (2006.01) |
| *A61K 45/06* | (2006.01) |
| *C12N 15/11* | (2006.01) |
| *A61K 35/28* | (2015.01) |

(52) U.S. Cl.
CPC ............ *C12N 15/113* (2013.01); *A61K 31/05* (2013.01); *A61K 31/132* (2013.01); *A61K 31/265* (2013.01); *A61K 31/352* (2013.01); *A61K 31/395* (2013.01); *A61K 31/4709* (2013.01); *A61K 31/519* (2013.01); *A61K 31/52* (2013.01); *A61K 31/565* (2013.01); *A61K 31/573* (2013.01); *A61K 31/704* (2013.01); *A61K 31/7048* (2013.01); *A61K 31/7088* (2013.01); *A61K 31/713* (2013.01); *A61K 38/1709* (2013.01); *A61K 45/06* (2013.01); *A61K 47/60* (2017.08); *A61K 47/6455* (2017.08); *A61K 48/0008* (2013.01); *A61K 48/0066* (2013.01); *C12N 15/111* (2013.01); *C12N 15/85* (2013.01); *A61K 35/28* (2013.01); *C12N 2310/14* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,208,479 A | 6/1980 | Zuk et al. | |
| 8,017,577 B2 | 9/2011 | Cooper et al. | |
| 10,654,910 B2 | 5/2020 | Spencer et al. | |
| 10,761,099 B2 | 9/2020 | Ziady et al. | |
| 2006/0142225 A1* | 6/2006 | McSwiggen | C07H 21/00 514/44 A |
| 2006/0148828 A1* | 7/2006 | Gianella-Borradori | A61K 31/4745 514/263.32 |
| 2006/0153808 A1* | 7/2006 | Cristofanilli | A61K 38/1709 424/93.2 |
| 2009/0264505 A1* | 10/2009 | Kay | A01K 67/0275 514/44 A |
| 2017/0042819 A1* | 2/2017 | Goomer | A61K 9/0019 |

OTHER PUBLICATIONS

Xu et al. (Journal of Neuro-Oncology (2012) 108:59-67) (Year: 2012).*
Kolodziej et al. (Oncol. Rep. (2015) 34(3):1549-56) (Year: 2015).*
Feng et al. (Tumor Biol. (2014) 35:4411-4417) (Year: 2014).*
Accurso FJ, et al., "Effect of VX-770 in Persons with Cystic Fibrosis and the G551D-*CFTR* Mutation." N Engl J Med, Nov. 18, 2010, 363(21):1991-2003, 13 pgs.
Albert PS, et al., "An Approach for Jointly Modeling Multivariate Longitudinal Measurements and Discrete Time-To-Event Data," Ann Appl Stat, 2010, 4(3):1517-1532, 16 pgs.
Asar O, et al., "mmm: An R package for analyzing multivariate longitudinal data with multivariate marginal models," Comput Methods Programs Biomed, 2013, 112(3):649-654, 6 pgs.
Brebner JA, et al., "Polyclonal free light chains: a biomarker of inflammatory disease or treatment target?" F1000 Med Rep, 2013, 5:4, 6 pgs.
Bundgaard, H., (ed.), *Design of Prodrugs*, Elsevier, Amsterdam, 1985, pp. 7-9, 21-24, 8 pgs.

(Continued)

*Primary Examiner* — J. E. Angell
(74) *Attorney, Agent, or Firm* — Frost Brown Todd LLC; Nicole M. Tepe

(57) ABSTRACT

Disclosed are methods for the enhancement of nucleic acid delivery systems. The methods may employ treatment with a compound and/or an RNAi molecule in combination with a nucleic acid to improve nucleic acid uptake into a cell. In particular, the disclosed methods may be useful for improved gene therapy techniques.

14 Claims, 5 Drawing Sheets

(56) References Cited

OTHER PUBLICATIONS

Chatterjee N, et al., "Constrained Maximum Likelihood Estimation for Model Calibration Using Summary-level Information from External Big Data Sources" J Am Stat Assoc, 2016, 111(513):107-117, 11 pgs.
Chen J, et al., "Dysfunction of Nrf-2 in CF Epithelia Leads to Excess Intracellular $H_2O_2$ and Inflammatory Cytokine Production," PLoS One, 2008, 3(10):e3367, 12 pgs.
Chen X, et al., "Nucleolin-Mediated Cellular Trafficking of DNA Nanoparticle Is Lipid Raft and Microtubule Dependent and Can Be Modulated by Glucocorticoid," Mol Ther, 2011, 19(1):93-102, 10 pgs.
Chipman HA, et al., "BART: Bayesian Additive Regression Trees," Ann Appl Stat, 2014, 23(1):42-59, 33 pgs.
Chirkova T, et al., "CX3CR1 is an important surface molecule for respiratory syncytial virus infection in human airway epithelial cells," J Gen Virol, 2015, 96:2543-2556, 14 pgs.
Chmiel J, et al., "The Effect of Sulforaphane in Broccoli Sprouts on Nrf2 Activation, Glutathione, Markers of Oxidative Stress, and Neutrophil Migration," Pediatr Pulmonol, 2012, 47(S35):250; 2012 Cystic Fibrosis Conference, Poster Session Abstract 82*, 1 pg.
Chromy, B.A., et al., "Proteomic Analysis of Human Serum by Two-Dimensional Differential Gel Electrophoresis after Depletion of High-Abundant Proteins," Journal of Proteome Research, 2004, 3:1120-1127, 8 pgs.
Chui, CK, et al., "Interpolation by Multivariate Splines," Math Comput, 1988, 51(183):203-218, 16 pgs.
Clancy JP, et al., "Personalized Medicine in Cystic Fibrosis: Dawning of a New Era," Am J Respir Crit Care Med, 2012, 186(7):593-597, 5 pgs.
Diggle PJ, et al., "Real-time monitoring of progression towards renal failure in primary care patients," Biostatistics, 2015, 16(3):522-536, 15 pgs.
Drumm ML, et al., "Genetic Variation and Clinical Heterogeneity in Cystic Fibrosis," Annu Rev Pathol, 2012, 7:267-282, 18 pgs.
Duan LL, et at., "Bayesian Ensemble Trees (BET) for Clustering and Prediction in Heterogeneous Data," J Comput Graph Stat, 2016, 25(3):748-761, 14 pgs.
Duan LL, et al., "Joint Hierarchical Gaussian Process Model with Application to Forecast in Medical Monitoring," 2014, eprint arXiv:1408.4660, 23 pgs.
Fieuws S, et al., "Predicting renal graft failure using multivariate longitudinal profiles," Biostatistics, 2008, 9(3):419-431, 13 pgs.
Fieuws S, et al., "Random-effects models for multivariate repeated measures," Stat Methods Med Res, Oct. 2007, 16(5):387-397, 11 pgs.
Fischer K, et al., "Biomarker Profiling by Nuclear Magnetic Resonance Spectroscopy for the Prediction of All-Cause Mortality: An Observational Study of 17,345 Persons," PLoS Med, Feb. 2014, 11(2):e1001606, 12 pgs.
Green, PJ, et al., "Nonparametric regression and generalized linear models: a roughness penalty approach," 1$^{st}$ ed. London, New York: Chapman & Hall, 1994, ix, 182 p. Table of Contents Only, 8 pgs.
Groot Kormelink, T., et al., "Immunoglobulin Free Light Chains Are Increased in Hypersensitivity Pneumonitis and Idiopathic Pulmonary Fibrosis," PLoS one, 2011, 6(9):e25392, 7 pgs.
Harun SN, et al., "A systematic review of studies examining the rate of lung function decline in patients with cystic fibrosis," Paediatr Respir Rev, 2016, 20:55-66, 12 pgs.
Hastie T, et al., *The Elements of Statistical Learning: Data Mining, Inference, and Prediction*, Second Ed., Springer Science + Business Media, LLC, New York, NY, 2009, (Table of Contents Only) 12 pgs.
Huang, L., et al., "Highly Selective Targeting of Hepatic Stellate Cells for Liver Fibrosis Treatment Using a D-Enantiomeric Peptide Ligand of Fn14 Identified by Mirror-Image mRNA Display," Mol Pharmaceutics, 2017, 14:1742-1753, 12 pgs.
James GM, et al., "Principal component models for sparse functional data," Biometrika, 2000, 87(3):587-602, 16 pgs.

Jiang C-R, et al., "Covariate Adjusted Functional Principal Components Analysis For Longitudinal Data," The Annals of Statistics, 2010, 38(2): 1194-1226, 34 pgs.
Kim PY, et al., "Identification of plasma Complement C3 as a potential biomarker for neuroblastoma using a quantitative proteomic approach," J Proteomics, 2014, 96:1-12, 12 pgs.
La Rosa PS, et al., "Hypothesis Testing and Power Calculations for Taxonomic-Based Human Microbiome Data," PLoS One, 2012, 7(12):e52078, 13 pgs.
Laguna TA, et al., "Sputum Desmosine During Hospital Admission for Pulmonary Exacerbation in Cystic Fibrosis," Chest, Dec. 2009, 136(6):1561-1568, 8 pgs.
Lancioni CL, et al., "*Mycobacterium tuberculosis* Lipoproteins Directly Regulate Human Memory CD4+ T Cell Activation via Toll-Like Receptors 1 and 2," Infect Immun, Feb. 2011, 79(2):663-673, 11 pgs.
Li Q, et al., "Rv2468c, a novel *Mycobacterium tuberculosis* protein that costimulates human CD4+ T cells through VLA-5," J Leukoc Biol, Feb. 2012, 91(2):311-20, 10 pgs.
Liou TG, et al., "Year-to-year changes in lung function in individuals with cystic fibrosis," J Cyst Fibros, 2010, 9(4):250-6, 7 pgs.
Nick JA, et al., "Blood mRNA biomarkers for detection of treatment response in acute pulmonary exacerbations of cystic fibrosis," Thorax, 2013, 68(10):929-937, 9 pgs.
Obuchowski NA, et al., "Sample Size Determination for Diagnostic Accuracy Studies Involving Binormal ROC Curve Indices," Stat Med, 1997, 16(13):1529-1542, 14 pgs.
Peila, C., et al., "Effects of Holder pasteurization on the protein profile of human milk," Italian journal of Pediatrics, 2016, 42:36, 8 pgs.
Peng, J., et al., "A Geometric Approach to Maximum Likelihood Estimation of the Functional Principal Components From Sparse Longitudinal Data," J Comput Graph Stat, 2009, 18(4):995-1015, Technical Report 2007a, 87 pgs.
Peng, J., Restricted MLE for Functional Principal Components Analysis (R package fpca) 2015. Available from: https://CRAN.R-project.org/package=fpca, 12 pgs.
Ramsay JO, et al., *Functional data analysis*, Second Ed., Springer Science + Business Media, Inc., New York., NY, 2005, p. 426, (Table of Contents only) 13 pgs.
Ratjen F, et al., "Effect of Azithromycin on Systemic Markers of Inflammation in Patients With Cystic Fibrosis Uninfected With *Pseudomonas aeruginosa*," Chest, 2012, 142(5):1259-1266, 8 pgs.
Rosenfeld M, et al., "Baseline Characteristics and Factors Associated With Nutritional and Pulmonary Status at Enrollment in the Cystic Fibrosis EPIC Observational Cohort," Pediatr Pulmonol, 2010, 45(9):934-944, 11 pgs.
Rosenfeld M, et al., "Decline in Lung Function Does not Predict Future Decline in Lung Function in Cystic Fibrosis Patients," Pediatr Pulmonol, 2015, 50(9):856-862, 7 pgs.
Sagel SD, et al., "Effect of Treatment of Cystic Fibrosis Pulmonary Exacerbations on Systemic Inflammation," Ann Am Thorac Soc, 2015, 12(5):708-717, 10 pgs.
Sagel SD, et al., "Validation of Candidate Serum Protein and Lipid Markers of Disease Severity in CF," Pediatr Pulmonol, 2014, 49(S38):288, 2014 Cystic Fibrosis Conference, Poster Session Abstract 205*, 1 pg.
Sanders DB, et al., "Failure to Recover to Baseline Pulmonary Function after Cystic Fibrosis Pulmonary Exacerbation," Am J Respir Crit Care Med, 2010, 182(5):627-632, 6 pgs.
Schluchter MD, et al., "Classifying Severity of Cystic Fibrosis Lung Disease Using Longitudinal Pulmonary Function Data," Am J Respir Crit Care Med, 2006, 174(7):780-786, 7 pgs.
Sinha C, et al., "PKA and actin play critical roles as downstream effectors in MRP4-mediated regulation of fibroblast migration," Cell Signal, 2015, 27(7):1345-1355, 11 pgs.
Sinha C, et al., "Capturing the Direct Binding of CFTR Correctors to CFTR by Using Click Chemistry," Chembiochem, 2015, 16:2017-2022, 6 pgs.
Slobodianik NH, et al., "Inflammatory biomarker profile in children with cystic fibrosis: preliminary study," Proc Nutr Soc, 3$^{rd}$ Interna-

(56) References Cited

OTHER PUBLICATIONS tional Immunonutrition Workshop; Session 4: Dietary strategies to prevent and mitigate inflammatory diseases, 2010, 69(3):354-356, 3 pgs.
Sun, W., et al., "Real-Time Imaging of Gene Delivery and Expression with DNA Nanoparticle Technologies," Chapter 33, In: Foote R., Lee J. (eds) Micro and Nano Technologies in Bioanalysis. Methods in Molecular Biology (Methods and Protocols), Humana Press, Totowa, NJ Methods Mol Biol, 2009, 544:525-546.
Szczesniak RD, et al., "A semiparametric approach to estimate rapid lung function decline in cystic fibrosis," Annals of Epidemiology, 2013, 23(12):771-777, 7 pgs.
Szczesniak RD, et al., "Phenotypes of Rapid Cystic Fibrosis Lung Disease Progression during Adolescence and Young Adulthood," American Journal of Respiratory and Critical Care Medicine, 2017, 196(4): 471-478, 8 pgs.
Szczesniak RD, et al., "Predicting Future Lung Function Decline in Cystic Fibrosis Patients: Statistical Methods and Clinical Connections," Pediatr Pulmonol, Letter to the Editor, 2016, 51(2):217-218, 2 pgs.
Tang Y, et al., "Developing Adaptive Personalized Therapy for Cystic Fibrosis Using Reinforcement Learning," Submitted to Ann Appl Stat, 2012, 28 pgs.
Taylor-Robinson D, et al., "Understanding the natural progression in %$FEV_1$ decline in patients with cystic fibrosis: a longitudinal study," Thorax, 2012, 67(10):860-866, 7 pgs.
Tibshirani RJ., "Regression Shrinkage and Selection via the Lasso," J R Statist Soc B, 1996, 58(1):267-288, 22 pgs.
Tucholska M, et al., "Human Serum Proteins Fractionated by Preparative Partition Chromatography Prior to LC-ESI-MS/MS," J Proteome Res, 2009, 8(3):1143-1155, 13 pgs.
Verbeke G, et al., "The analysis of multivariate longitudinal data: A review," Stat Methods Med Res, 2014, 23(1):42-59, 18 pgs.
Wainwright CE, et al., "Lumacaftor-Ivacaftor in Patients with Cystic Fibrosis Homozygous for Phe508del *CFTR*," N Engl J Med, 2015, 373(3):220-231, 12 pgs.
Wang J, et al., "Measuring the impact of apnea and obesity on circadian activity patterns using functional linear modeling of actigraphy data," J Circadian Rhythms, 2011, 9(1):11, 10 pgs.
Wang X, et al., "Hsp90 Cochaperone Ahal Downregulation Rescues Misfolding of CFTR in Cystic Fibrosis," Cell, 2006, 127(4):803-815, 13 pgs.
Wolff, M.E., (ed.), Burger's Medicinal Chemistry and Drug Discovery, 5th ed., 1995, pp. 172-178, 949-982, 41 pgs.
Yanagisawa K, et al., "Proteomic patterns of tumour subsets in non-small-cell lung cancer," Lancet, 2003, 362(9382):433-439, 7 pgs.
Yao, F., et al., "Functional Data Analysis for Sparse Longitudinal Data," Journal of the American Statistical Association, 2005, 100(470):577-590, 14 pgs.
Zeitzer JM, et al., "Phenotyping Apathy in Individuals With Alzheimer Disease Using Functional Principal Component Analysis," Am J Geriatr Psychiatry, 2013, 21(4):391-397, 12 pgs.
Zemanick ET, et al., "Inflammation and Airway Microbiota During Cystic Fibrosis Pulmonary Exacerbations," PLoS One, 2013, 8(4):e62917, 13 pgs.
Ziady AG, et al., "Interaction with CREB binding protein modulates the activities of Nrf2 and NF-κB in cystic fibrosis airway epithelial cells," Am J Physiol Lung Cell Mol Physiol, 2012, 302(11):L1221-L1231, 11 pgs.
Ziady AG, et al., "Protein Sequencing with Tandem Mass Spectrometry," Chapter 21, James Weifu Lee, et al., Eds. *Micro and Nano Technologies in Bioanalysis*, Methods Mol Biol, 2009, 544:325-341, 17 pgs.
Ziady AG, et al., "Proteomic Analyses of BALF Reveal Potential Biomarkers and Suggest Altered Lipid, Cyclic Nucleotide, and Iron Metabolism in Young CF Children Versus Disease Controls," Pediatr Pulmonol, 2013, 48(S36):277-278, 2013 Cystic Fibrosis Conference, Poster Session Abstract 204*, 2 pgs.
Ziady AG, et al., "Proteomic Analyses of Serum From CF Patients With Mild or Severe Disease Reveal the Differential Expression of Proteins That Regulate the Differentiation of Cartilage, Myeloid Leukocytes, and Intestinal Epithelia" Pediatr Pulmonol, 2014, 49(S38):288, 2014 Cystic Fibrosis Conference, Poster Session Abstract 206*, 1 pg.
International Search Report and Written Opinion dated Aug. 10, 2020 for Application No. PCT/US2020/030401, 10 pgs.
U.S. Appl. No. 16/922,119, filed Jul. 7, 2020, by Ziady et al., entitled: "Compositions and Methods for Treatment of Lung Function.".
Ahmed, H., et al., "Emerging Gene Therapies for Genetic Hearing Loss," J Assoc Res Otolaryngol, Aug. 16, 2017, 22 pgs.
Cai, X., et al., "Gene delivery to mitotic and postmitotic photoreceptors via compacted DNA nanoparticles results in improved phenotype in a mouse model of retinitis pigmentosa," FASEB J, Apr. 2010, 24(4):1178-91, 25 pgs.
Ding, X.Q., et al., "Ocular delivery of compacted DNA-nanoparticles does not elicit toxicity in the mouse retina," PLoS One, 2009, 4(10):e7410, 11 pgs.
Farjo, R., et al., "Efficient non-viral ocular gene transfer with compacted DNA nanoparticles," PLoS One, 2006, 1:e38, 12 pgs.
Fletcher, A.M., et al., "Transgene expression in the striatum following intracerebral injections of DNA nanoparticles encoding for human glial cell line-derived neurotrophic factor," Neuroscience, Oct. 27, 2011. 194:220-6, 7 pgs.
Huang, J., et al., "CRISPR Editing in Biological and Biomedical Investigation," J Cell Physiol, Aug. 8, 2017, 19 pgs.
Koirala, A., et al., "S/MAR-containing DNA nanoparticles promote persistent RPE gene expression and improvement in RPE65-associated LCA," Hum Mol Genet, Apr. 15, 2013, 22(8):1632-42, 11 pgs.
Konstan, M.W., et al., "Compacted DNA nanoparticles administered to the nasal mucosa of cystic fibrosis subjects are safe and demonstrate partial to complete cystic fibrosis transmembrane regulator reconstitution," Hum. Gene Ther., Dec. 2004, 15(12):1255-69, 15 pgs.
Naso, M.F., et al., "Adeno-Associated Virus (AAV) as a Vector for Gene Therapy," Bio Drugs, Jul. 1, 2017, 31:317-334, 18 pgs.
Yurek, D.M., et al., "Compacted DNA nanoparticle gene transfer of GDNF to the rat striatum enhances the survival of grafted fetal dopamine neurons," Cell Transplant., 2009, 18(10):1183-96, 15 pgs.
Yurek, D.M., et al., "DNA Nanoparticles: Detection of Long-term Transgene Activity in Brain Using Bioluminescence Imaging," Mol. Imaging, Apr. 26, 2011, 10(5):327-339, 12 pgs.
Yurek, D.M., et al., "Long-term transgene expression in the central nervous system using DNA nanoparticles," Mol. Ther., Apr. 2009, 17(4):641-50, 14 pgs.
Zhang, X., et al., "CRISPR/Cas9 system: a powerful technology for in vivo and ex vivo gene therapy," Sci. China Life Sci, May 2017, 60(5):468-75, 8 pgs.
Ziady, A.G., et al., "Current prospects for gene therapy of cystic fibrosis," Curr Opin Pharmacol, Oct. 2006, 6(5):515-21, 7 pgs.
Ziady, A.G., et al., "Functional evidence CFTR gene transfer in nasal epithelium of cystic fibrosis mice in Vivo following luminal application of DNA complexes targeted to the serpin-enzyme complex receptor," Mol. Ther., Apr. 2002, 5(4):413-9, 7 pgs.
Ziady, A.G., et al., "Non-viral gene transfer therapy for cystic fibrosis," Expert Opin Biol Ther, Jun. 2003, 3(3):449-58, 10 pgs.
U.S. Appl. No. 62/381,237, filed Aug. 30, 2016.

* cited by examiner

COMPOSITIONS AND METHODS FOR NUCLEIC ACID TRANSFER

CROSS REFERENCE TO RELATED APPLICATION

This application claims priority to and benefit of U.S. Provisional Patent Application Ser. No. 62/381,237, filed Aug. 30, 2016, entitled "Method for Enhancing Nucleic Acid Transfer," the contents of which are incorporated by reference in its entirety for all purposes.

GOVERNMENT SUPPORT CLAUSE

This invention was made with government support under EB023800 awarded by the National Institutes of Health. The government has certain rights in the invention.

BACKGROUND

Transfer of nucleic acids, including double and single stranded DNA as well as RNA, into eukaryotic cells is the most essential step of any gene transfer, repair, or editing technology. Transfer of nucleic acids may be accomplished using many types of delivery vehicles, including cationic lipids, viral vectors and nucleic acid nanoparticles condensed with cationic polymers such as poly lysine or polyethyleneimine. However, significant costs involved in the preparation of these materials present a significant limitation in their usage as both research tools and translational applications such as gene therapy. Further, efficacy of nucleic acid transfer with or without modification of the vector remains an area in need of improvement. The instant disclosure seeks to address one or more of the aforementioned needs in the art.

BRIEF SUMMARY

Disclosed are methods for the enhancement of nucleic acid delivery systems. The methods may employ treatment with a compound and/or an RNAi molecule in combination with, for example, prior to or concurrent with, administration of a nucleic acid to improve nucleic acid uptake into a cell. In particular, the disclosed methods may be useful for improved gene therapy techniques in which a disclosed RNAi and/or a disclosed compound may be administered prior to or concurrently with the gene therapy delivery vehicle containing a nucleic acid.

DETAILED DESCRIPTION OF THE INVENTION

Definitions

Figure 1:
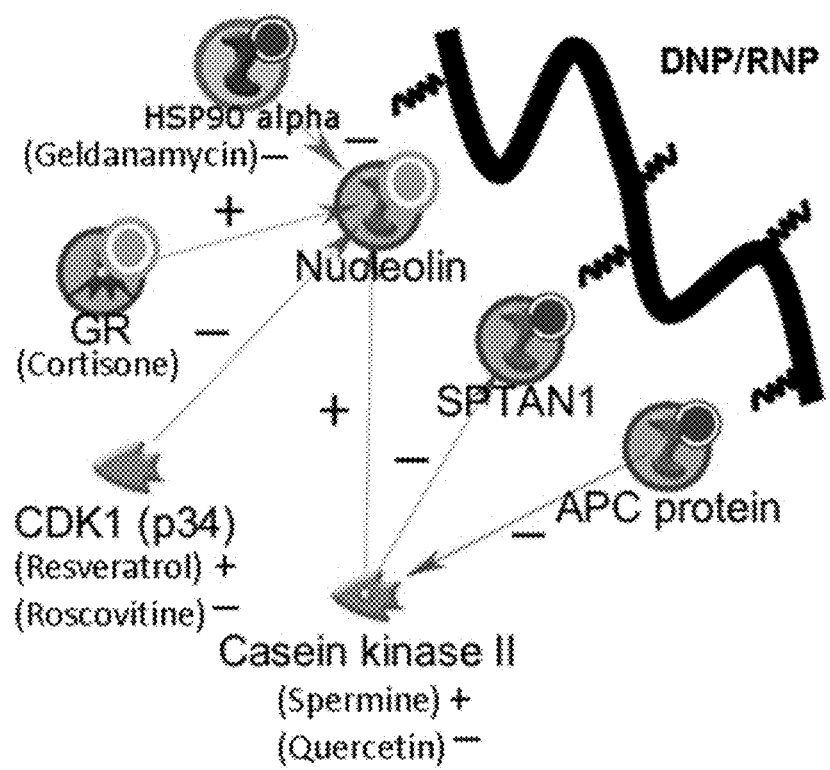
FIG. 1 is a schematic of partial NNP (DNP and RNP) interactome including nucleoin, APC, and SPTAN1, which were identified by MS analysis of 2 gel bands from DNP and RNP pull downs not present in bead alone control. Lighter color circles connote interactions that enhance NNP-mediated gene transfer, while darker circles connote interactions that inhibit. (+) or (−) along arrows connote impact on interactions with DNP. (+) or (−) by pharmacological agents reflect impact on the activation of GR, CDK1, or CKII. For example, while cortisone would increase nucleolin at the membrane via GR (10), spermine would increase it through stimulation of CKII mediated phosphorylation of nucleolin. Pull downs initially conducted in primary hepatocytes and repeated three times in wd-AECs for 2 non-CF and 3 CF subjects. This DNP interactome was observed in all the hepatocyte and CF and non-CF wd-AEC studies.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, for example, within 5-fold, and or for example, within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt," as used herein, refers to a formulation of a compound that does not cause significant irritation to an organism to which it is administered and does not abrogate the biological activity and properties of the compounds described herein. As used herein, the disclosed compounds also include pharmaceutically acceptable salts thereof.

The terms "composition" or "pharmaceutical composition," as used herein, refers to a mixture of at least one compound or RNAi as disclosed herein, with at least one and optionally more than one other pharmaceutically acceptable chemical components, such as carriers, stabilizers, diluents, dispersing agents, suspending agents, thickening agents, and/or excipients.

The term "carrier" applied to pharmaceutical compositions of the disclosure refers to a diluent, excipient, or vehicle with which an active compound (e.g., dextromethorphan) is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like.

The term "NNP" refers to a Nucleic acid Nano Particle: a complex of DNA or RNA with polymers of lysines (15-45 lysines long)

The term "DNP" refers to a DNA Nanoparticle

The term "RNP" refers to a RNA Nanoparticle

The term "Interactome" refers to the whole set of molecular interactions in a particular cell. The term specifically refers to physical interactions among molecules (such as those among proteins, also known as protein—protein interactions) but can also describe sets of indirect interactions among genes (genetic interactions).

The term "APC" refers to an adenomatous polyposis coli protein

The term "wd-AECs" refer to well-differentiated airway epithelial cells.

The term "SPTAN1" refers to Alpha II-spectrin, also known as

Spectrin alpha chain, a protein that in humans is encoded by the SPTAN1 gene. Alpha II-spectrin is expressed in a variety of tissues, and is highly expressed in cardiac muscle at Z-disc structures, costameres and at the sarcolemma membrane.

The term "GR" refers to a glucocorticoid receptor

The term "CDK1" refers to cyclin dependent kinase 1

The term "CKII" refers to casein kinase II

The term "Spermine" refers to a polyamine involved in cellular metabolism found in all eukaryotic cells.

The term "shRNA" refers to a small hairpin RNA or short hairpin RNA (shRNA) is an artificial RNA molecule with a tight hairpin turn that can be used to silence target gene expression via RNA interference (RNAi)

Disclosed herein are methods for the enhancement of nucleic acid delivery systems by combination treatment with one or more compounds as disclosed herein and/or one or more RNAi molecules as disclosed herein. For example, the disclosed methods may be used with delivery of a nucleic acid such as a gene, a gene fragment, a fragment containing an active portion of a protein encoded by a gene, or the like. Further examples of nucleic acids that may be delivered include nucleic acid components of the CRISPR/CAS9, or short nucleic acids, such as microRNA or DNA or RNA oligonucleotides. The disclosed RNAi molecules and/or compounds may be administered to an individual in need of administration of a nucleic acid prior to administration of a nucleic acid delivery system, or concurrently with the administration of a nucleic acid delivery system.

The method, in certain aspects, may comprise the steps of
contacting a cell with an RNAi molecule or an active agent. The RNAi molecule or active agent may be in an amount sufficient to inhibit synthesis of one or more proteins that inhibit nucleic acid delivery vehicle uptake; and
contacting the eukaryotic cell with a nucleic acid delivery vehicle.

The cell may be, for example, a eukaryotic cell, derived from a human being.

In one aspect, a method of treating an individual is disclosed. The individual may be one in which administration a therapeutically effective amount of a protein may be advantageous to reversal, prevention, or amelioration of a disease state. The delivery of a protein may be achieved via administration of a gene, or portion of a gene that encodes an active portion of a protein, that may be subsequently expressed in the individual to provide a functional protein or functional protein fragment in a therapeutically effective amount. In this aspect, the method may comprise the steps of administering an RNAi that inhibits expression of a gene encoding a protein selected from a protein of Table 1 and/or a compound selected from Table 2 or 3, concurrently, before, or after administration of a drug delivery vehicle containing the nucleic acid that encodes the gene, or in some instances, the active portion of a gene, of interest.

The amount of compound and/or RNAi necessary to effect the methods of the instant disclosure may be determined by one of ordinary skill in the art. The dose administered to a subject, particularly a human, may be sufficient to effect the desired response in the subject over a reasonable period of time. The dose may be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. For example, the compounds may be therapeutically effective at low doses. Exemplary dosage ranges may be from about 0.001 mM, or less, to about 100 mM, or more, or from about 0.01, 0.05, 0.1, 0.5, 0.6, 0.7, 0.8, or 0.9 mM, to about 1, 2, 3, 4, 5, 6, 7, 8, 9, 10, 20, 30, 40 50, 60, 70, 80, 90 or 100 mM. Accordingly, the compounds may be generally administered in low doses.

In one aspect, the gene is the CF gene, and the individual in need of treatment is an individual having cystic fibrosis.

In one aspect, the RNAi molecule may be one that inhibits expression of a gene encoding a protein selected from a protein of Table 1.

TABLE 1

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| P04114 | APOB | Apolipoprotein B-100 (Apo B-100) [Cleaved into: Apolipoprotein B-48 (Apo B-48)] |
| P29536 | LMOD1 | Leiomodin-1 (64 kDa autoantigen 1D) (64 kDa autoantigen 1D3) (64 kDa autoantigen D1) (Leiomodin, muscle form) (Smooth muscle leiomodin) (SM-Lmod) (Thyroid-associated ophthalmopathy autoantigen) |
| P68104 | EEF1A1 EEF1A EF1A LENG7 | Elongation factor 1-alpha 1 (EF-1-alpha-1) (Elongation factor Tu) (EF-Tu) (Eukaryotic elongation factor 1 A-1) (eEF1A-1) (Leukocyte receptor cluster member 7) |
| O19680 | | Pot. HLA-DP-alpha 1 (Aa −31 to +2) (441 is 1st base in codon) (Fragment) |
| P46939 | UTRN DMDL DRP1 | Utrophin (Dystrophin-related protein 1) (DRP-1) |
| P08590 | MYL3 | Myosin light chain 3 (Cardiac myosin light chain 1) (CMLC1) (Myosin light chain 1, slow-twitch muscle B/ventricular isoform) (MLC1SB) (Ventricular myosin alkali light chain) (Ventricular myosin light chain 1) (VLC1) (Ventricular/slow twitch myosin alkali light chain) (MLC-1V/sb) |
| P22695 | UQCRC2 | Cytochrome b-c1 complex subunit 2, mitochondrial (Complex III subunit 2) (Core protein II) (Ubiquinol-cytochrome-c reductase complex core protein 2) |
| Q16763 | UBE2S E2EPF OK/SW-cl.73 | Ubiquitin-conjugating enzyme E2 S (EC 2.3.2.23) (E2 ubiquitin-conjugating enzyme S) (E2-EPF) (Ubiquitin carrier protein S) (Ubiquitin-conjugating enzyme E2-24 kDa) (Ubiquitin-conjugating enzyme E2-EPF5) (Ubiquitin-protein ligase S) |
| P00451 | F8 F8C | Coagulation factor VIII (Antihemophilic factor) (AHF) (Procoagulant component) [Cleaved into: Factor VIIIa heavy chain, 200 kDa isoform; Factor VIIIa heavy chain, 92 kDa isoform; Factor VIII B chain; Factor VIIIa light chain] |
| P52272 | HNRNPM HNRPM NAGR1 | Heterogeneous nuclear ribonucleoprotein M (hnRNP M) |
| P60660 | MYL6 | Myosin light polypeptide 6 (17 kDa myosin light chain) (LC17) (Myosin light chain 3) (MLC-3) (Myosin light chain alkali 3) (Myosin light chain A3) (Smooth muscle and nonmuscle myosin light chain alkali 6) |
| P25054 | APC DP2.5 | Adenomatous polyposis coli protein (Protein APC) (Deleted in polyposis 2.5) |
| P23458 | JAK1 JAK1A JAK1B | Tyrosine-protein kinase JAK1 (EC 2.7.10.2) (Janus kinase 1) (JAK-1) |
| P13533 | MYH6 MYHCA | Myosin-6 (Myosin heavy chain 6) (Myosin heavy chain, cardiac muscle alpha isoform) (MyHC-alpha) |
| P61247 | RPS3A FTE1 MFTL | 40S ribosomal protein S3a (Small ribosomal subunit protein eS1) (v-fos transformation effector protein) (Fte-1) |
| Q08379 | GOLGA2 | Golgin subfamily A member 2 (130 kDa cis-Golgi matrix protein) (GM130) (GM130 autoantigen) (Golgin-95) |
| P41219 | PRPH NEF4 PRPH1 | Peripherin (Neurofilament 4) |
| Q99729 | HNRNPAB ABBP1 HNRPAB | Heterogeneous nuclear ribonucleoprotein A/B (hnRNP A/B) (APOBEC1-binding protein 1) (ABBP-1) |
| P11277 | SPTB SPTB1 | Spectrin beta chain, erythrocytic (Beta-I spectrin) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| P33981 | TTK MPS1 MPS1L1 | Dual specificity protein kinase TTK (EC 2.7.12.1) (Phosphotyrosine picked threonine-protein kinase) (PYT) |
| P11021 | HSPA5 GRP78 | 78 kDa glucose-regulated protein (GRP-78) (Endoplasmic reticulum lumenal Ca(2+)-binding protein grp78) (Heat shock 70 kDa protein 5) (Immunoglobulin heavy chain-binding protein) (BiP) |
| Q15552 | tb protein | CACCC box-binding protein |
| P62913 | RPL11 | 60S ribosomal protein L11 (CLL-associated antigen KW-12) (Large ribosomal subunit protein uL5) |
| P38919 | EIF4A3 DDX48 KIAA0111 | Eukaryotic initiation factor 4A-III (eIF-4A-III) (eIF4A-III) (EC 3.6.4.13) (ATP-dependent RNA helicase DDX48) (ATP-dependent RNA helicase eIF4A-3) (DEAD box protein 48) (Eukaryotic initiation factor 4A-like NUK-34) (Eukaryotic translation initiation factor 4A isoform 3) (Nuclear matrix protein 265) (NMP 265) (hNMP 265) [Cleaved into: Eukaryotic initiation factor 4A-III, N-terminally processed] |
| Q12905 | ILF2 NF45 PRO3063 | Interleukin enhancer-binding factor 2 (Nuclear factor of activated T-cells 45 kDa) |
| Q14978 | NOLC1 KIAA0035 NS5ATP13 | Nucleolar and coiled-body phosphoprotein 1 (140 kDa nucleolar phosphoprotein) (Nopp140) (Hepatitis C virus NS5A-transactivated protein 13) (HCV NS5A-transactivated protein 13) (Nucleolar 130 kDa protein) (Nucleolar phosphoprotein p130) |
| P20929 | NEB | Nebulin |
| Q16296 | 4R-MAP2 | Microtubule-associated protein (Fragment) |
| P33991 | MCM4 CDC21 | DNA replication licensing factor MCM4 (EC 3.6.4.12) (CDC21 homolog) (P1-CDC21) |
| P49454 | CENPF | Centromere protein F (CENP-F) (AH antigen) (Kinetochore protein CENPF) (Mitosin) |
| Q14008 | CKAP5 KIAA0097 | Cytoskeleton-associated protein 5 (Colonic and hepatic tumor overexpressed gene protein) (Ch-TOG) |
| Q14839 | CHD4 | Chromodomain-helicase-DNA-binding protein 4 (CHD-4) (EC 3.6.4.12) (ATP-dependent helicase CHD4) (Mi-2 autoantigen 218 kDa protein) (Mi2-beta) |
| P55017 | SLC12A3 NCC TSC | Solute carrier family 12 member 3 (Na—Cl cotransporter) (NCC) (Na—Cl symporter) (Thiazide-sensitive sodium-chloride cotransporter) |
| Q92835 | INPP5D SHIP SHIP1 | Phosphatidylinositol 3,4,5-trisphosphate 5-phosphatase 1 (EC 3.1.3.86) (Inositol polyphosphate-5-phosphatase of 145 kDa) (SIP-145) (SH2 domain-containing inositol 5'-phosphatase 1) (SH2 domain-containing inositol phosphatase 1) (SHIP-1) (p150Ship) (hp51CN) |
| Q15269 | PWP2 PWP2H | Periodic tryptophan protein 2 homolog |
| P20585 | MSH3 DUC1 DUG | DNA mismatch repair protein Msh3 (hMSH3) (Divergent upstream protein) (DUP) (Mismatch repair protein 1) (MRP1) |
| Q05086 | UBE3A E6AP EPVE6AP HPVE6A | Ubiquitin-protein ligase E3A (EC 2.3.2.26) (E6AP ubiquitin-protein ligase) (HECT-type ubiquitin transferase E3A) (Human papillomavirus E6-associated protein) (Oncogenic protein-associated protein E6-AP) (Renal carcinoma antigen NY-REN-54) |
| Q92922 | SMARCC1 BAF155 | SWI/SNF complex subunit SMARCC1 (BRG1-associated factor 155) (BAF155) (SWI/SNF complex 155 kDa subunit) (SWI/SNF-related matrix-associated actin-dependent regulator of chromatin subfamily C member 1) |
| P62807 | HIST1H2B C H2BFL; HIST1H2B E H2BFH; HIST1H2B F H2BFG; HIST1H2B G H2BFA; HIST1H2BI H2BFK | Histone H2B type 1-C/E/F/G/I (Histone H2B.1 A) (Histone H2B.a) (H2B/a) (Histone H2B.g) (H2B/g) (Histone H2B.h) (H2B/h) (Histone H2B.k) (H2B/k) (Histone H2B.l) (H2B/l) |
| Q92800 | EZH1 KIAA0388 | Histone-lysine N-methyltransferase EZH1 (EC 2.1.1.43) (ENX-2) (Enhancer of zeste homolog 1) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| P78549 | NTHL1 NTH1 OCTS3 | Endonuclease III-like protein 1 (hNTH1) (EC 3.2.2.—) (EC 4.2.99.18) (Bifunctional DNA N-glycosylase/DNA-(apurinic or apyrimidinic site) lyase) (DNA glycosylase/AP lyase) |
| Q12789 | GTF3C1 | General transcription factor 3C polypeptide 1 (TF3C-alpha) (TFIIIC box B-binding subunit) (Transcription factor IIIC 220 kDa subunit) (TFIIIC 220 kDa subunit) (TFIIIC220) (Transcription factor IIIC subunit alpha) |
| O14686 | KMT2D ALR MLL2 MLL4 | Histone-lysine N-methyltransferase 2D (Lysine N-methyltransferase 2D) (EC 2.1.1.43) (ALL1-related protein) (Myeloid/lymphoid or mixed-lineage leukemia protein 2) |
| Q13304 | GPR17 | Uracil nucleotide/cysteinyl leukotriene receptor (UDP/CysLT receptor) (G-protein coupled receptor 17) (P2Y-like receptor) (R12) |
| Q9UQB3 | CTNND2 NPRAP | Catenin delta-2 (Delta-catenin) (GT24) (Neural plakophilin-related ARM-repeat protein) (NPRAP) (Neurojungin) |
| P30519 | HMOX2 HO2 | Heme oxygenase 2 (HO-2) (EC 1.14.14.18) |
| O60437 | PPL KIAA0568 | Periplakin (190 kDa paraneoplastic pemphigus antigen) (195 kDa cornified envelope precursor protein) |
| Q15413 | RYR3 HBRR | Ryanodine receptor 3 (RYR-3) (RyR3) (Brain ryanodine receptor-calcium release channel) (Brain-type ryanodine receptor) (Type 3 ryanodine receptor) |
| Q13618 | CUL3 KIAA0617 | Cullin-3 (CUL-3) |
| O75691 | UTP20 DRIM | Small subunit processome component 20 homolog (Down-regulated in metastasis protein) (Novel nucleolar protein 73) (NNP73) (Protein Key-1A6) |
| O80743 | T13D8.9 | T13D8.9 protein |
| P38159 | RBMX HNRPG RBMXP1 | RNA-binding motif protein, X chromosome (Glycoprotein p43) (Heterogeneous nuclear ribonucleoprotein G) (hnRNP G) [Cleaved into: RNA-binding motif protein, X chromosome, N-terminally processed] |
| O75081 | CBFA2T3 MTG16 MTGR2 ZMYND4 | Protein CBFA2T3 (MTG8-related protein 2) (Myeloid translocation gene on chromosome 16 protein) (hMTG16) (Zinc finger MYND domain-containing protein 4) |
| O95153 | TSPOAP1 BZRAP1 KIAA0612 RBP1 RIMBP1 | Peripheral-type benzodiazepine receptor-associated protein 1 (PRAX-1) (Peripheral benzodiazepine receptor-interacting protein) (PBR-IP) (RIMS-binding protein 1) (RIM-BP1) (TSPO-associated protein 1) |
| P63267 | ACTG2 ACTA3 ACTL3 ACTSG | Actin, gamma-enteric smooth muscle (Alpha-actin-3) (Gamma-2-actin) (Smooth muscle gamma-actin) |
| P18754 | RCC1 CHC1 | Regulator of chromosome condensation (Cell cycle regulatory protein) (Chromosome condensation protein 1) |
| Q5T081 | RCC1 CHC1 hCG_27809 | CHC1 protein (Regulator of chromosome condensation 1 isoform 1) (Regulator of chromosome condensation 1, isoform CRA_b) |
| P13639 | EEF2 EF2 | Elongation factor 2 (EF-2) |
| Q16695 | HIST3H3 H3FT | Histone H3.1t (H3/t) (H3t) (H3/g) |
| A8K401 | PHB hCG_29613 | Prohibitin, isoform CRA_a (cDNA FLJ78511, highly similar to Homo sapiens prohibitin (PHB), mRNA) (cDNA, FLJ93035, Homo sapiens prohibitin (PHB), mRNA) |
| P35232 | PHB | Prohibitin |
| Q53FV0 | | Prohibitin variant (Fragment) |
| P83731 | RPL24 | 60S ribosomal protein L24 (60S ribosomal protein L30) (Large ribosomal subunit protein eL24) |
| V9HW01 | HEL-S-310 | Epididymis secretory protein Li 310 |
| A0A024RCA7 | RPLP2 hCG_1778304 | Ribosomal protein, large, P2, isoform CRA_a |
| P05387 | RPLP2 D11S2243E RPP2 | 60S acidic ribosomal protein P2 (Large ribosomal subunit protein P2) (Renal carcinoma antigen NY-REN-44) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| P46783 | RPS10 | 40S ribosomal protein S10 (Small ribosomal subunit protein eS10) |
| P62280 | RPS11 | 40S ribosomal protein S11 (Small ribosomal subunit protein uS17) |
| P62277 | RPS13 | 40S ribosomal protein S13 (Small ribosomal subunit protein uS15) |
| P08708 | RPS17 RPS17L | 40S ribosomal protein S17 (Small ribosomal subunit protein eS17) |
| A8K517 | RPS23 hCG_38189 | Ribosomal protein S23, isoform CRA_a (cDNA FLJ77921, highly similar to *Homo sapiens* ribosomal protein S23 (RPS23), mRNA) (cDNA, FLJ92033, *Homo sapiens* ribosomal protein S23 (RPS23), mRNA) |
| P62266 | RPS23 | 40S ribosomal protein S23 (Small ribosomal subunit protein uS12) |
| P62851 | RPS25 | 40S ribosomal protein S25 (Small ribosomal subunit protein eS25) |
| B2R491 | RPS4X hCG_18634 | 40S ribosomal protein S4 |
| P62701 | RPS4X CCG2 RPS4 SCAR | 40S ribosomal protein S4, X isoform (SCR10) (Single copy abundant mRNA protein) (Small ribosomal subunit protein eS4) |
| P62241 | RPS8 OK/SW-cl.83 | 40S ribosomal protein S8 (Small ribosomal subunit protein eS8) |
| Q5JR94 | RPS8 hCG_2031852 | 40S ribosomal protein S8 |
| P12755 | SKI | Ski oncogene (Proto-oncogene c-Ski) |
| A0A1L1UHR1 | | Sperm binding protein 1a |
| B3KTS5 | | cDNA FLJ38670 fis, clone HSYRA2000190, highly similar to Voltage-dependent anion-selective channel protein 1 |
| P21796 | VDAC1 VDAC | Voltage-dependent anion-selective channel protein 1 (VDAC-1) (hVDAC1) (Outer mitochondrial membrane protein porin 1) (Plasmalemmal porin) (Porin 31HL) (Porin 31HM) |
| P25490 | YY1 INO80S | Transcriptional repressor protein YY1 (Delta transcription factor) (INO80 complex subunit S) (NF-E1) (Yin and yang 1) (YY-1) |
| Q99996 | AKAP9 AKAP350 AKAP450 KIAA0803 | A-kinase anchor protein 9 (AKAP-9) (A-kinase anchor protein 350 kDa) (AKAP 350) (hgAKAP 350) (A-kinase anchor protein 450 kDa) (AKAP 450) (AKAP 120-like protein) (Centrosome- and Golgi-localized PKN-associated protein) (CG-NAP) (Protein hyperion) (Protein kinase A-anchoring protein 9) (PRKA9) (Protein yotiao) |
| P16402 | HIST1H1D H1F3 | Histone H1.3 (Histone H1c) (Histone H1s-2) |
| Q96GY0 | ZC2HC1A C8orf70 FAM164A CGI-62 | Zinc finger C2HC domain-containing protein 1A |
| P02545 | LMNA LMN1 | Prelamin-A/C [Cleaved into: Lamin-A/C (70 kDa lamin) (Renal carcinoma antigen NY-REN-32)] |
| P20700 | LMNB1 LMN2 LMNB | Lamin-B1 |
| P14550 | AKR1A1 ALDR1 ALR | Alcohol dehydrogenase [NADP(+)] (EC 1.1.1.2) (Aldehyde reductase) (Aldo-keto reductase family 1 member A1) |
| V9HWI0 | HEL-S-165mP HEL-S-6 | Epididymis secretory protein Li 6 (Epididymis secretory sperm binding protein Li 165mP) |
| A0PJH2 | ATP5H | ATP5H protein (Fragment) |
| O75947 | ATP5H My032 | ATP synthase subunit d, mitochondrial (ATPase subunit d) |
| P19105 | MYL12A MLCB MRLC3 RLC | Myosin regulatory light chain 12A (Epididymis secretory protein Li 24) (HEL-S-24) (MLC-2B) (Myosin RLC) (Myosin regulatory light chain 2, nonsarcomeric) (Myosin regulatory light chain MRLC3) |
| A0A0G2JS52 | | Uncharacterized protein (Fragment) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| V9H0H3 | | Gag-Pro-Pol-Env protein |
| P17096 | HMGA1 HMGIY | High mobility group protein HMG-I/HMG-Y (HMG-I(Y)) (High mobility group AT-hook protein 1) (High mobility group protein A1) (High mobility group protein R) |
| O46577 | COX4I1 COX4 | Cytochrome c oxidase subunit 4 isoform 1, mitochondrial (Cytochrome c oxidase polypeptide IV) (Cytochrome c oxidase subunit IV isoform 1) (COX IV-1) (Fragment) |
| Q9UIG0 | BAZ1B WBSC10 WBSCR10 WBSCR9 WSTF | Tyrosine-protein kinase BAZ1B (EC 2.7.10.2) (Bromodomain adjacent to zinc finger domain protein 1B) (Williams syndrome transcription factor) (Williams-Beuren syndrome chromosomal region 10 protein) (Williams-Beuren syndrome chromosomal region 9 protein) (hWALp2) |
| Q9UHD8 | SEPT9 KIAA0991 MSF | Septin-9 (MLL septin-like fusion protein MSF-A) (MLL septin-like fusion protein) (Ovarian/Breast septin) (Ov/Br septin) (Septin D1) |
| P62270 | Rps18 | 40S ribosomal protein S18 (Ke-3) (Ke3) |
| Q561N5 | Rps18 mCG_23000 | MCG23000, isoform CRA_b (Putative uncharacterized protein) (Ribosomal protein S18) |
| Q9NWS8 | RMND1 C6orf96 | Required for meiotic nuclear division protein 1 homolog |
| P31942 | HNRNPH3 HNRPH3 | Heterogeneous nuclear ribonucleoprotein H3 (hnRNP H3) (Heterogeneous nuclear ribonucleoprotein 2H9) (hnRNP 2H9) |
| Q9NZR2 | LRP1B LRPDIT | Low-density lipoprotein receptor-related protein 1B (LRP-1B) (Low-density lipoprotein receptor-related protein-deleted in tumor) (LRP-DIT) |
| Q16891 | IMMT HMP MIC60 MINOS2 PIG4 PIG52 | MICOS complex subunit MIC60 (Cell proliferation-inducing gene 4/52 protein) (Mitochondrial inner membrane protein) (Mitofilin) (p87/89) |
| A4D1N4 | CHCHD3 hCG_20148 41 tcag7.1158 | MICOS complex subunit |
| Q9NX63 | CHCHD3 MIC19 MINOS3 | MICOS complex subunit MIC19 (Coiled-coil-helix-coiled-coil-helix domain-containing protein 3) |
| Q6NTF9 | RHBDD2 RHBDL7 | Rhomboid domain-containing protein 2 |
| Q6P1M9 | ARMCX5 | Armadillo repeat-containing X-linked protein 5 |
| O00148 | DDX39A DDX39 | ATP-dependent RNA helicase DDX39A (EC 3.6.4.13) (DEAD box protein 39) (Nuclear RNA helicase URH49) |
| Q6UY01 | LRRC31 UNQ9367/PRO34156 | Leucine-rich repeat-containing protein 31 |
| Q8IYT3 | CCDC170 C6orf97 | Coiled-coil domain-containing protein 170 |
| Q2L6I2 | ABCF1 ABC50 hCG_26012 | ABC50 protein (ATP-binding cassette, sub-family F (GCN20), member 1) (ATP-binding cassette, sub-family F (GCN20), member 1, isoform CRA_a) |
| Q8NE71 | ABCF1 ABC50 | ATP-binding cassette sub-family F member 1 (ATP-binding cassette 50) (TNF-alpha-stimulated ABC protein) |
| Q99459 | CDC5L KIAA0432 PCDC5RP | Cell division cycle 5-like protein (Cdc5-like protein) (Pombe cdc5-related protein) |
| P35580 | MYH10 | Myosin-10 (Cellular myosin heavy chain, type B) (Myosin heavy chain 10) (Myosin heavy chain, non-muscle IIb) (Non-muscle myosin heavy chain B) (NMMHC-B) (Non-muscle myosin heavy chain IIb) (NMMHC II-b) (NMMHC-IIB) |
| P50914 | RPL14 | 60S ribosomal protein L14 (CAG-ISL 7) (Large ribosomal subunit protein eL14) |
| Q9C093 | SPEF2 KIAA1770 KPL2 | Sperm flagellar protein 2 (Protein KPL2) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
| --- | --- | --- |
| P08729 | KRT7 SCL | Keratin, type II cytoskeletal 7 (Cytokeratin-7) (CK-7) (Keratin-7) (K7) (Sarcolectin) (Type-II keratin Kb7) |
| Q9BTQ7 | | Similar to ribosomal protein L23 (Fragment) |
| Q96RT7 | TUBGCP6 GCP6 KIAA1669 | Gamma-tubulin complex component 6 (GCP-6) |
| Q5M8Q0 | Rpl15 mCG_10029 | Ribosomal protein L15 |
| Q9CZM2 | Rpl15 | 60S ribosomal protein L15 |
| Q9BS75 | KLHL20 hCG_23698 | KLHL20 protein (Kelch-like 20 (*Drosophila*), isoform CRA_a) |
| P82970 | HMGN5 NSBP1 | High mobility group nucleosome-binding domain-containing protein 5 (Nucleosome-binding protein 1) |
| A0A024QZW2 | NOL7 hCG_37417 | Nucleolar protein 7, 27 kDa, isoform CRA_a |
| Q9UMY1 | NOL7 C6orf90 NOP27 | Nucleolar protein 7 (Nucleolar protein of 27 kDa) |
| P62907 | Rpl10a | 60S ribosomal protein L10a |
| P78527 | PRKDC HYRC HYRC1 | DNA-dependent protein kinase catalytic subunit (DNA-PK catalytic subunit) (DNA-PKcs) (EC 2.7.11.1) (DNPK1) (p460) |
| B4E1W3 | | cDNA FLJ51732, highly similar to Peroxisomal NADH pyrophosphatase NUDT12 (EC 3.6.1.22) |
| Q9BQG2 | NUDT12 | Peroxisomal NADH pyrophosphatase NUDT12 (EC 3.6.1.22) (Nucleoside diphosphate-linked moiety X motif 12) (Nudix motif 12) |
| P46779 | RPL28 | 60S ribosomal protein L28 (Large ribosomal subunit protein eL28) |
| P22626 | HNRNPA2B1 HNRPA2B1 | Heterogeneous nuclear ribonucleoproteins A2/B1 (hnRNP A2/B1) |
| Q96Q15 | SMG1 ATX KIAA0421 LIP | Serine/threonine-protein kinase SMG1 (SMG-1) (hSMG-1) (EC 2.7.11.1) (61E3.4) (Lambda/iota protein kinase C-interacting protein) (Lambda-interacting protein) |
| A0A024R4M0 | RPS9 hCG_2009111 | 40S ribosomal protein S9 (Ribosomal protein S9, isoform CRA_a) |
| P46781 | RPS9 | 40S ribosomal protein S9 (Small ribosomal subunit protein uS4) |
| Q96T23 | RSF1 HBXAP XAP8 | Remodeling and spacing factor 1 (Rsf-1) (HBV pX-associated protein 8) (Hepatitis B virus X-associated protein) (p325 subunit of RSF chromatin-remodeling complex) |
| P60709 | ACTB | Actin, cytoplasmic 1 (Beta-actin) [Cleaved into: Actin, cytoplasmic 1, N-terminally processed] |
| Q96RL1 | UIMC1 RAP80 RXRIP110 | BRCA1-A complex subunit RAP80 (Receptor-associated protein 80) (Retinoid X receptor-interacting protein 110) (Ubiquitin interaction motif-containing protein 1) |
| Q96A11 | GAL3ST3 | Galactose-3-O-sulfotransferase 3 (Gal3ST-3) (EC 2.8.2.—) (Beta-galactose-3-O-sulfotransferase 3) (Gal3ST3) (Gal-beta-1, 3-GalNAc 3'-sulfotransferase 3) |
| P62847 | RPS24 | 40S ribosomal protein S24 (Small ribosomal subunit protein eS24) |
| Q9NSI6 | BRWD1 C21orf107 WDR9 | Bromodomain and WD repeat-containing protein 1 (WD repeat-containing protein 9) |
| A0A024R1X8 | JUP hCG_1771506 | Junction plakoglobin, isoform CRA_a |
| Q96QZ7 | MAGI1 AIP3 BAIAP1 BAP1 TNRC19 | Membrane-associated guanylate kinase, WW and PDZ domain-containing protein 1 (Atrophin-1-interacting protein 3) (AIP-3) (BAI1-associated protein 1) (BAP-1) (Membrane-associated guanylate kinase inverted 1) (MAGI-1) (Trinucleotide repeat-containing gene 19 protein) (WW domain-containing protein 3) (WWP3) |
| A8K4C8 | RPL13 hCG_1723872 | 60S ribosomal protein L13 |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
| --- | --- | --- |
| P26373 | RPL13<br>BBC1<br>OK/SW-cl.46 | 60S ribosomal protein L13 (Breast basic conserved protein 1) (Large ribosomal subunit protein eL13) |
| P46019 | PHKA2<br>PHKLA<br>PYK | Phosphorylase b kinase regulatory subunit alpha, liver isoform (Phosphorylase kinase alpha L subunit) |
| O60506 | SYNCRIP<br>HNRPQ<br>NSAP1 | Heterogeneous nuclear ribonucleoprotein Q (hnRNP Q) (Glycine- and tyrosine-rich RNA-binding protein) (GRY-RBP) (NS1-associated protein 1) (Synaptotagmin-binding, cytoplasmic RNA-interacting protein) |
| Q96Q42 | ALS2<br>ALS2CR6<br>KIAA1563 | Alsin (Amyotrophic lateral sclerosis 2 chromosomal region candidate gene 6 protein) (Amyotrophic lateral sclerosis 2 protein) |
| Q8IYJ3 | SYTL1<br>SLP1<br>SB146 | Synaptotagmin-like protein 1 (Exophilin-7) (Protein JFC1) |
| A0A024RDH8 | RPL34<br>hCG_2027853 | Ribosomal protein L34, isoform CRA_a |
| P49207 | RPL34 | 60S ribosomal protein L34 (Large ribosomal subunit protein eL34) |
| Q9P2M7 | CGN<br>KIAA1319 | Cingulin |
| Q96BT3 | CENPT<br>C16orf56<br>ICEN22 | Centromere protein T (CENP-T) (Interphase centromere complex protein 22) |
| Q0VF96 | CGNL1<br>JACOP<br>KIAA1749 | Cingulin-like protein 1 (Junction-associated coiled-coil protein) (Paracingulin) |
| Q96M95 | CCDC42<br>CCDC42A | Coiled-coil domain-containing protein 42 |
| P52597 | HNRNPF<br>HNRPF | Heterogeneous nuclear ribonucleoprotein F (hnRNP F) (Nucleolin-like protein mcs94-1) [Cleaved into: Heterogeneous nuclear ribonucleoprotein F, N-terminally processed] |
| O96008 | TOMM40<br>C19orf1<br>PEREC1<br>TOM40 | Mitochondrial import receptor subunit TOM40 homolog (Protein Haymaker) (Translocase of outer membrane 40 kDa subunit homolog) (p38.5) |
| Q96BS4 | FBL | FBL protein (Putative uncharacterized protein) (Fragment) |
| Q9H501 | ESF1<br>ABTAP<br>C20orf6<br>HDCMC28P | ESF1 homolog (ABT1-associated protein) |
| Q6PHZ2 | Camk2d<br>Kiaa4163 | Calcium/calmodulin-dependent protein kinase type II subunit delta (CaM kinase II subunit delta) (CaMK-II subunit delta) (EC 2.7.11.17) |
| Q07020 | RPL18 | 60S ribosomal protein L18 (Large ribosomal subunit protein eL18) |
| Q8TF72 | SHROOM3<br>KIAA1481<br>SHRML<br>MSTP013 | Protein Shroom3 (Shroom-related protein) (hShrmL) |
| Q8TE73 | DNAH5<br>DNAHC5<br>HL1<br>KIAA1603 | Dynein heavy chain 5, axonemal (Axonemal beta dynein heavy chain 5) (Ciliary dynein heavy chain 5) |
| O75475 | PSIP1<br>DFS70<br>LEDGF<br>PSIP2 | PC4 and SFRS1-interacting protein (CLL-associated antigen KW-7) (Dense fine speckles 70 kDa protein) (DPS 70) (Lens epithelium-derived growth factor) (Transcriptional coactivator p75/p52) |
| E9KL44 | | Epididymis tissue sperm binding protein Li 14m |
| P40939 | HADHA<br>HADH | Trifunctional enzyme subunit alpha, mitochondrial (78 kDa gastrin-binding protein) (TP-alpha) [Includes: Long-chain enoyl-CoA hydratase (EC 4.2.1.17); Long chain 3-hydroxyacyl-CoA dehydrogenase (EC 1.1.1.211)] |
| Q9HB09 | BCL2L12<br>BPR | Bcl-2-like protein 12 (Bcl2-L-12) (Bcl2-related proline-rich protein) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| O75367 | H2AFY MACROH2 A1 | Core histone macro-H2A.1 (Histone macroH2A1) (mH2A1) (Histone H2A.y) (H2A/y) (Medulloblastoma antigen MU-MB-50.205) |
| Q8N6Z2 | MTRF1 hCG_32761 | MTRF1 protein (Mitochondrial translational release factor 1, isoform CRA_b) (Peptide chain release factor 1, mitochondrial) |
| Q8TCU4 | ALMS1 KIAA0328 | Alstrom syndrome protein 1 |
| A0JNW5 | UHRF1BP1 L KIAA0701 | UHRF1-binding protein 1-like |
| O75643 | SNRNP200 ASCC3L1 HELIC2 KIAA0788 | U5 small nuclear ribonucleoprotein 200 kDa helicase (EC 3.6.4.13) (Activating signal cointegrator 1 complex subunit 3-like 1) (BRR2 homolog) (U5 snRNP-specific 200 kDa protein) (U5-200KD) |
| A7E2E1 | SMARCA4 hCG_29955 | SWI/SNF related, matrix associated, actin dependent regulator of chromatin, subfamily a, member 4 (SWI/SNF related, matrix associated, actin dependent regulator of chromatin, subfamily a, member 4, isoform CRA_a) (cDNA FLJ77531, highly similar to Homo sapiens SWI/SNF related, matrix associated, actin dependent regulator of chromatin, subfamily a, member 4 (SMARCA4), mRNA) |
| P51532 | SMARCA4 BAF190A BRG1 SNF2B SNF2L4 | Transcription activator BRG1 (EC 3.6.4.—) (ATP-dependent helicase SMARCA4) (BRG1-associated factor 190A) (BAF190A) (Mitotic growth and transcription activator) (Protein BRG-1) (Protein brahma homolog 1) (SNF2-beta) (SWI/SNF-related matrix-associated actin-dependent regulator of chromatin subfamily A member 4) |
| O00418 | EEF2K | Eukaryotic elongation factor 2 kinase (eEF-2 kinase) (eEF-2K) (EC 2.7.11.20) (Calcium/calmodulin-dependent eukaryotic elongation factor 2 kinase) |
| Q96CN4 | EVI5L | EVI5-like protein (Ecotropic viral integration site 5-like protein) |
| Q9H8V3 | ECT2 | Protein ECT2 (Epithelial cell-transforming sequence 2 oncogene) |
| Q5T3F8 | TMEM63B C6orf110 | CSC1-like protein 2 (Transmembrane protein 63B) |
| Q8NAJ6 | | cDNA FLJ35251 fis, clone PROST2003635, weakly similar to MULTIFUNCTIONAL AMINOACYL-TRNA SYNTHETASE |
| A0A0C4DG40 | SYNE1 | Nesprin-1 |
| Q8NF91 | SYNE1 C6orf98 KIAA0796 KIAA1262 KIAA1756 MYNE1 | Nesprin-1 (Enaptin) (KASH domain-containing protein 1) (KASH1) (Myocyte nuclear envelope protein 1) (Myne-1) (Nuclear envelope spectrin repeat protein 1) (Synaptic nuclear envelope protein 1) (Syne-1) |
| Q8TDI0 | CHD5 KIAA0444 | Chromodomain-helicase-DNA-binding protein 5 (CHD-5) (EC 3.6.4.12) (ATP-dependent helicase CHD5) |
| Q9NU22 | MDN1 KIAA0301 | Midasin (MIDAS-containing protein) |
| Q8WXH0 | SYNE2 KIAA1011 NUA | Nesprin-2 (KASH domain-containing protein 2) (KASH2) (Nuclear envelope spectrin repeat protein 2) (Nucleus and actin connecting element protein) (Protein NUANCE) (Synaptic nuclear envelope protein 2) (Syne-2) |
| Q9Y277 | VDAC3 | Voltage-dependent anion-selective channel protein 3 (VDAC-3) (hVDAC3) (Outer mitochondrial membrane protein porin 3) |
| Q96QE3 | ATAD5 C17orf41 FRAG1 | ATPase family AAA domain-containing protein 5 (Chromosome fragility-associated gene 1 protein) |
| Q9BXJ9 | NAA15 GA19 NARG1 NATH TBDN100 | N-alpha-acetyltransferase 15, NatA auxiliary subunit (Gastric cancer antigen Ga19) (N-terminal acetyltransferase) (NMDA receptor-regulated protein 1) (Protein tubedown-1) (Tbdn100) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| Q8IUE6 | HIST2H2AB | Histone H2A type 2-B |
| Q5TZA2 | CROCC KIAA0445 | Rootletin (Ciliary rootlet coiled-coil protein) |
| A0A024RAS2 | H2AFJ hCG_1639762 | Histone H2A |
| Q9BTM1 | H2AFJ | Histone H2A.J (H2a/j) |
| Q8NEN9 | PDZD8 PDZK8 | PDZ domain-containing protein 8 (Sarcoma antigen NY-SAR-84/NY-SAR-104) |
| Q14683 | SMC1A DXS423E KIAA0178 SB1.8 SMC1 SMC1L1 | Structural maintenance of chromosomes protein 1A (SMC protein 1A) (SMC-1-alpha) (SMC-1A) (Sb1.8) |
| Q68EN4 | SMC1A | SMC1A protein (Fragment) |
| Q7Z7G8 | VPS13B CHS1 COH1 KIAA0532 | Vacuolar protein sorting-associated protein 13B (Cohen syndrome protein 1) |
| Q7Z7A1 | CNTRL CEP1 CEP110 | Centriolin (Centrosomal protein 1) (Centrosomal protein of 110 kDa) (Cep110) |
| O95613 | PCNT KIAA0402 PCNT2 | Pericentrin (Kendrin) (Pericentrin-B) |
| A0A140VK14 | | Testicular secretory protein Li 14 |
| P49448 | GLUD2 GLUDP1 | Glutamate dehydrogenase 2, mitochondrial (GDH 2) (EC 1.4.1.3) |
| Q5VTT5 | MYOM3 | Myomesin-3 (Myomesin family member 3) |
| Q7Z612 | | Acidic ribosomal phosphoprotein P1 |
| O00567 | NOP56 NOL5A | Nucleolar protein 56 (Nucleolar protein 5A) |
| Q9Y2X3 | NOP58 NOL5 NOP5 HSPC120 | Nucleolar protein 58 (Nucleolar protein 5) |
| A0A0C4DFX4 | | Uncharacterized protein (Fragment) |
| Q6ZNL4 | FLJ00279 | FLJ00279 protein (Fragment) |
| Q6ZWK7 | | cDNA FLJ16045 fis, clone CTONG2000042, weakly similar to ALPHA-2-MACROGLOBULIN |
| Q7Z388 | DPY19L4 | Probable C-mannosyltransferase DPY19L4 (EC 2.4.1.—) (Dpy-19-like protein 4) (Protein dpy-19 homolog 4) |
| Q5T9S5 | CCDC18 | Coiled-coil domain-containing protein 18 (Sarcoma antigen NY-SAR-24) |
| Q6ZV73 | FGD6 KIAA1362 ZFYVE24 | FYVE, RhoGEF and PH domain-containing protein 6 (Zinc finger FYVE domain-containing protein 24) |
| P25705 | ATP5A1 ATP5A ATP5AL2 ATPM | ATP synthase subunit alpha, mitochondrial |
| P42285 | SKIV2L2 DOB1 KIAA0052 Mtr4 | Superkiller viralicidic activity 2-like 2 (EC 3.6.4.13) (ATP-dependent RNA helicase DOB1) (ATP-dependent RNA helicase SKIV2L2) (TRAMP-like complex helicase) |
| Q00325 | SLC25A3 PHC OK/SW-cl.48 | Phosphate carrier protein, mitochondrial (Phosphate transport protein) (PTP) (Solute carrier family 25 member 3) |
| P62753 | RPS6 OK/SW-cl.2 | 40S ribosomal protein S6 (Phosphoprotein NP33) (Small ribosomal subunit protein eS6) |
| Q9BW34 | EEF1D | EEF1D protein (Fragment) |
| Q5K651 | SAMD9 C7orf5 DRIF1 KIAA2004 OEF1 | Sterile alpha motif domain-containing protein 9 (SAM domain-containing protein 9) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
| --- | --- | --- |
| Q6W6M6 | | Antigen MLAA-44 |
| Q5T0F9 | CC2D1B KIAA1836 | Coiled-coil and C2 domain-containing protein 1B (Five prime represser element under dual repression-binding protein 2) (FRE under dual repression-binding protein 2) (Freud-2) |
| P26641 | EEF1G EF1G PRO1608 | Elongation factor 1-gamma (EF-1-gamma) (eEF-1B gamma) |
| Q00839 | HNRNPU HNRPU SAFA U21.1 | Heterogeneous nuclear ribonucleoprotein U (hnRNP U) (Scaffold attachment factor A) (SAF-A) (p120) (pp120) |
| Q9Y4C4 | MFHAS1 MASL1 | Malignant fibrous histiocytoma-amplified sequence 1 (Malignant fibrous histiocytoma-amplified sequence with leucine-rich tandem repeats 1) |
| P16050 | ALOX15 LOG15 | Arachidonate 15-lipoxygenase (15-LOX) (15-LOX-1) (EC 1.13.11.33) (12/15-lipoxygenase) (Arachidonate 12-lipoxygenase, leukocyte-type) (12-LOX) (EC 1.13.11.31) (Arachidonate omega-6 lipoxygenase) |
| P16383 | GCFC2 C2orf3 GCF TCF9 | GC-rich sequence DNA-binding factor 2 (GC-rich sequence DNA-binding factor) (Transcription factor 9) (TCF-9) |
| P36578 | RPL4 RPL1 | 60S ribosomal protein L4 (60S ribosomal protein L1) (Large ribosomal subunit protein uL4) |
| O76081 | RGS20 RGSZ1 ZGAP1 | Regulator of G-protein signaling 20 (RGS20) (Gz-selective GTPase-activating protein) (G(z)GAP) (Gz-GAP) (Regulator of G-protein signaling Z1) (Regulator of Gz-selective protein signaling 1) |
| Q9Y6N9 | USH1C AIE75 | Harmonin (Antigen NY-CO-38/NY-CO-37) (Autoimmune enteropathy-related antigen AIE-75) (Protein PDZ-73) (Renal carcinoma antigen NY-REN-3) (Usher syndrome type-1C protein) |
| Q15149 | PLEC PLEC1 | Plectin (PCN) (PLTN) (Hemidesmosomal protein 1) (HD1) (Plectin-1) |
| O60333 | KIF1B KIAA0591 KIAA1448 | Kinesin-like protein KIF1B (Klp) |
| O60462 | NRP2 VEGF165R2 | Neuropilin-2 (Vascular endothelial cell growth factor 165 receptor 2) |
| Q7Z3T9 | DKFZp686J1169 | Neuropilin |
| Q5THJ4 | VPS13D KIAA0453 | Vacuolar protein sorting-associated protein 13D |
| Q9NRZ9 | HELLS PASG SMARCA6 Nbla10143 | Lymphoid-specific helicase (EC 3.6.4.—) (Proliferation-associated SNF2-like protein) (SWI/SNF2-related matrix-associated actin-dependent regulator of chromatin subfamily A member 6) |
| Q96A08 | HIST1H2BA TSH2B | Histone H2B type 1-A (Histone H2B, testis) (TSH2B.1) (hTSH2B) (Testis-specific histone H2B) |
| Q6UB99 | ANKRD11 ANCO1 | Ankyrin repeat domain-containing protein 11 (Ankyrin repeat-containing cofactor 1) |
| I6L9F7 | HIST1H2BM | Histone H2B (Fragment) |
| P02538 | KRT6A K6A KRT6D | Keratin, type II cytoskeletal 6A (Cytokeratin-6A) (CK-6A) (Cytokeratin-6D) (CK-6D) (Keratin-6A) (K6A) (Type-II keratin Kb6) (allergen Hom s 5) |
| Q6KC79 | NIPBL IDN3 | Nipped-B-like protein (Delangin) (SCC2 homolog) |
| Q8NBU5 | ATAD1 FNP001 | ATPase family AAA domain-containing protein 1 (EC 3.6.1.3) (Thorase) |
| E5KLM2 | | Mitochondrial dynamin-like 120 kDa protein |
| Q15772 | SPEG APEG1 KIAA1297 | Striated muscle preferentially expressed protein kinase (EC 2.7.11.1) (Aortic preferentially expressed protein 1) (APEG-1) |
| O14490 | DLGAP1 DAP1 GKAP | Disks large-associated protein 1 (DAP-1) (Guanylate kinase-associated protein) (hGKAP) (PSD-95/SAP90-binding protein 1) (SAP90/PSD-95-associated protein 1) (SAPAP1) |
| Q5JSL3 | DOCK11 ZIZ2 | Dedicator of cytokinesis protein 11 (Activated Cdc42-associated guanine nucleotide exchange factor) (ACG) (Zizimin-2) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| Q5VU43 | PDE4DIP CMYA2 KIAA0454 KIAA0477 MMGL | Myomegalin (Cardiomyopathy-associated protein 2) (Phosphodiesterase 4D-interacting protein) |
| Q658X5 | DKFZp666 F1010 | Putative uncharacterized protein DKFZp666F1010 (Fragment) |
| Q658W4 | DKFZp666 M0710 | Putative uncharacterized protein DKFZp666M0710 (Fragment) |
| Q63HR1 | DKFZp686 P17171 | Putative uncharacterized protein DKFZp686P17171 |
| Q5VWT5 | ARAP C1orf168 | Activation-dependent, raft-recruited ADAP-like phosphoprotein |
| Q92614 | MYO18A CD245 KIAA0216 MYSPDZ | Unconventional myosin-XVIIIa (Molecule associated with JAK3 N-terminus) (MAJN) (Myosin containing a PDZ domain) (Surfactant protein receptor SP-R210) (SP-R210) |
| A0A024R4A0 | NCL hCG_33980 | Nucleolin, isoform CRA_b |
| B3KM80 | NCL hCG_33980 | Nucleolin, isoform CRA_c (cDNA FLJ10452 fis, clone NT2RP1000966, highly similar to NUCLEOLIN) |
| P19338 | NCL | Nucleolin (Protein C23) |
| P35527 | KRT9 | Keratin, type I cytoskeletal 9 (Cytokeratin-9) (CK-9) (Keratin-9) (K9) |
| Q5T655 | CFAP58 C10orf80 CCDC147 | Cilia- and flagella-associated protein 58 (Coiled-coil domain-containing protein 147) |
| Q5TAX3 | ZCCHC11 KIAA0191 TUT4 | Terminal uridylyltransferase 4 (TUTase 4) (EC 2.7.7.52) (Zinc finger CCHC domain-containing protein 11) |
| Q9Y6I7 | WSB1 SWIP1 | WD repeat and SOCS box-containing protein 1 (WSB-1) (SOCS box-containing WD protein SWiP-1) |
| Q9HC77 | CENPJ CPAP LAP LIP1 | Centromere protein J (CENP-J) (Centrosomal P4.1-associated protein) (LAG-3-associated protein) (LYST-interacting protein 1) |
| Q5H8C1 | FREM1 C9orf143 C9orf145 C9orf154 | FRAS1-related extracellular matrix protein 1 (Protein QBRICK) |
| Q8N5G2 | TMEM57 | Macoilin (Transmembrane protein 57) |
| Q58F05 | NARG1 | NARG1 protein (Fragment) |
| Q59HE3 | | Calpastatin isoform a variant (Fragment) |
| Q59GX9 | | Ribosomal protein L5 variant (Fragment) |
| Q59FF1 | | Insulin-like growth factor binding protein 2 variant (Fragment) |
| O75116 | ROCK2 KIAA0619 | Rho-associated protein kinase 2 (EC 2.7.11.1) (Rho kinase 2) (Rho-associated, coiled-coil-containing protein kinase 2) (Rho-associated, coiled-coil-containing protein kinase II) (ROCK-II) (p164 ROCK-2) |
| Q53HW2 | | 60S acidic ribosomal protein P0 (Fragment) |
| Q53HR5 | | Elongation factor 1-alpha (Fragment) |
| P14136 | GFAP | Glial fibrillary acidic protein (GFAP) |
| Q562R1 | ACTBL2 | Beta-actin-like protein 2 (Kappa-actin) |
| A0A024R2G2 | FANCD2 hCG_18114 43 | Fanconi anemia, complementation group D2, isoform CRA_b |
| Q9BXW9 | FANCD2 FACD | Fanconi anemia group D2 protein (Protein FACD2) |
| Q86XH1 | IQCA1 IQCA | IQ and AAA domain-containing protein 1 |
| A1XBS5 | FAM92A FAM92A1 | Protein FAM92A |
| Q9P273 | TENM3 KIAA1455 ODZ3 TNM3 | Teneurin-3 (Ten-3) (Protein Odd Oz/ten-m homolog 3) (Tenascin-M3) (Ten-m3) (Teneurin transmembrane protein 3) |
| Q9P2K1 | CC2D2A KIAA1345 | Coiled-coil and C2 domain-containing protein 2A |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
| --- | --- | --- |
| Q96BT1 | C3orf49 | Putative uncharacterized protein C3orf49 |
| P09651 | HNRNPA1 HNRPA1 | Heterogeneous nuclear ribonucleoprotein A1 (hnRNP A1) (Helix-destabilizing protein) (Single-strand RNA-binding protein) (hnRNP core protein A1) [Cleaved into: Heterogeneous nuclear ribonucleoprotein A1, N-terminally processed] |
| Q9P225 | DNAH2 DNAHC2 DNHD3 KIAA1503 | Dynein heavy chain 2, axonemal (Axonemal beta dynein heavy chain 2) (Ciliary dynein heavy chain 2) (Dynein heavy chain domain-containing protein 3) |
| Q4KM60 | Rpl10a Serpina6 | Ribosomal protein (Fragment) |
| Q32Q62 | RSL1D1 | RSL1D1 protein (Fragment) |
| Q9H611 | PIF1 C15orf20 | ATP-dependent DNA helicase PIF1 (EC 3.6.4.12) (DNA repair and recombination helicase PIF1) (PIF1/RRM3 DNA helicase-like protein) |
| Q86Y46 | KRT73 K6IRS3 KB36 KRT6IRS3 | Keratin, type II cytoskeletal 73 (Cytokeratin-73) (CK-73) (Keratin-73) (K73) (Type II inner root sheath-specific keratin-K6irs3) (Type-II keratin Kb36) |
| Q0QEN7 B3KU66 | ATP5B | ATP synthase subunit beta (EC 3.6.3.14) (Fragment) cDNA FLJ39263 fis, clone OCBBF2009571, highly similar to ATP-dependent RNA helicase A (EC 3.6.1.—) |
| Q08211 | DHX9 DDX9 LKP NDH2 | ATP-dependent RNA helicase A (RHA) (EC 3.6.4.13) (DEAH box protein 9) (Leukophysin) (LKP) (Nuclear DNA helicase II) (NDH II) |
| O15078 | CEP290 BBS14 KIAA0373 NPHP6 | Centrosomal protein of 290 kDa (Cep290) (Bardet-Biedl syndrome 14 protein) (Cancer/testis antigen 87) (CT87) (Nephrocystin-6) (Tumor antigen se2-2) |
| Q05BJ6 | CEP290 | CEP290 protein |
| Q92538 | GBF1 KIAA0248 | Golgi-specific brefeldin A-resistance guanine nucleotide exchange factor 1 (BFA-resistant GEF 1) |
| Q4G0J3 | LARP7 HDCMA18P | La-related protein 7 (La ribonucleoprotein domain family member 7) (P-TEFb-interaction protein for 7SK stability) (PIP7S) |
| Q15397 | PUM3 cPERP-C KIAA0020 PUF-A XTP5 | Pumilio homolog 3 (HBV X-transactivated gene 5 protein) (HBV XAg-transactivated protein 5) (Minor histocompatibility antigen HA-8) (HLA-HA8) |
| Q7RTY7 | OVCH1 | Ovochymase-1 (EC 3.4.21.—) |
| Q5SPB7 | ino80 si:ch211-244p18.3 | INO80 complex subunit |
| Q9Y3V2 | RWDD3 RSUME | RWD domain-containing protein 3 (RWD domain-containing sumoylation enhancer) (RSUME) |
| Q9HCR9 | PDE11A | Dual 3',5'-cyclic-AMP and -GMP phosphodiesterase 11A (EC 3.1.4.35) (EC 3.1.4.53) (cAMP and cGMP phosphodiesterase 11A) |
| Q9NR48 | ASH1L KIAA1420 KMT2H | Histone-lysine N-methyltransferase ASH1L (EC 2.1.1.43) (ASH1-like protein) (huASH1) (Absent small and homeotic disks protein 1 homolog) (Lysine N-methyltransferase 2H) |
| Q09428 | ABCC8 HRINS SUR SUR1 | ATP-binding cassette sub-family C member 8 (Sulfonylurea receptor 1) |
| Q5JU67 | CFAP157 C9orf117 | Cilia- and flagella-associated protein 157 |
| D3DR32 | MPHOSPH1 hCG_23744 | M-phase phosphoprotein 1, isoform CRA_a |
| G5E9G0 | RPL3 ASC-1 hCG_2015191 | 60S ribosomal protein L3 (Ribosomal protein L3, isoform CRA_e) |
| D3DS91 | AKAP6 hCG_1812123 | A kinase (PRKA) anchor protein 6, isoform CRA_b |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| A0A0A7M1X5 | LMNB2<br>hCG_2004338 | Lamin B2, isoform CRA_b (Lamin B3) |
| A0A024R5M9 | NUMA1<br>hCG_2017131 | Nuclear mitotic apparatus protein 1, isoform CRA_a |
| Q4G0X9 | CCDC40<br>KIAA1640 | Coiled-coil domain-containing protein 40 |
| D3DTT5 | TBKBP1<br>hCG_1813987 | TBK1 binding protein 1, isoform CRA_a |
| G5E972 | TMPO<br>hCG_2015322 | Lamina-associated polypeptide 2, isoforms beta/gamma (Thymopoietin, isoform CRA_d) |
| D6W5D1 | KIAA1212<br>hCG_1817741 | KIAA1212, isoform CRA_a |
| U3KQK0 | HIST1H2BN<br>hCG_1743059 | Histone H2B |
| D6RGI3 | SEPT11<br>hCG_24410 | Septin 11, isoform CRA_b (Septin-11) |
| B4DDB6 | HNRPA3<br>hCG_2005824 | Heterogeneous nuclear ribonucleoprotein A3, isoform CRA_a (cDNA FLJ52659, highly similar to Heterogeneous nuclear ribonucleoprotein A3) (cDNA, FLJ79333, highly similar to Heterogeneous nuclear ribonucleoprotein A3) |
| Q8TE76 | MORC4<br>ZCW4<br>ZCWCC2 | MORC family CW-type zinc finger protein 4 (Zinc finger CW-type coiled-coil domain protein 2) (Zinc finger CW-type domain protein 4) |
| Q8NCM8 | DYNC2H1<br>DHC1B<br>DHC2<br>DNCH2<br>DYH1B<br>KIAA1997 | Cytoplasmic dynein 2 heavy chain 1 (Cytoplasmic dynein 2 heavy chain) (Dynein Cytoplasmic heavy chain 2) (Dynein heavy chain 11) (hDHC11) (Dynein heavy chain isotype 1B) |
| Q6PIF6 | MYO7B | Unconventional myosin-VIIb |
| Q8NB66 | UNC13C | Protein unc-13 homolog C (Munc13-3) |
| A0A1U9X7W7 |  | HSPA1L |
| P34931 | HSPA1L | Heat shock 70 kDa protein 1-like (Heat shock 70 kDa protein 1L) (Heat shock 70 kDa protein 1-Hom) (HSP70-Hom) |
| A4D0S4 | LAMB4 | Laminin subunit beta-4 (Laminin beta-1-related protein) |
| Q8N309 | LRRC43 | Leucine-rich repeat-containing protein 43 |
| Q8TDW7 | FAT3<br>CDHF15<br>KIAA1989 | Protocadherin Fat 3 (hFat3) (Cadherin family member 15) (FAT tumor suppressor homolog 3) |
| A5WVL9 | dapk1<br>si:ch211-66i11.1 | Death-associated protein kinase (Death-associated protein kinase 1) |
| P05141 | SLC25A5<br>ANT2 | ADP/ATP translocase 2 (ADP, ATP carrier protein 2) (ADP, ATP carrier protein, fibroblast isoform) (Adenine nucleotide translocate 2) (ANT 2) (Solute carrier family 25 member 5) [Cleaved into: ADP/ATP translocase 2, N-terminally processed] |
| Q6NVC0 | SLC25A5 | SLC25A5 protein (Fragment) |
| P12236 | SLC25A6<br>ANT3<br>CDABP0051 | ADP/ATP translocase 3 (ADP, ATP carrier protein 3) (ADP, ATP carrier protein, isoform T2) (ANT 2) (Adenine nucleotide translocator 3) (ANT 3) (Solute carrier family 25 member 6) [Cleaved into: ADP/ATP translocase 3, N-terminally processed] |
| Q6I9V5 | SLC25A6<br>hCG_1746794 | SLC25A6 protein (Solute carrier family 25 (Mitochondrial carrier adenine nucleotide translocator), member 6) (cDNA, FLJ92654, highly similar to *Homo sapiens* solute carrier family 25 (mitochondrial carrier; adenine nucleotide translocator), member 6 (SLC25A6), mRNA) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
| --- | --- | --- |
| Q0VGD6 | HNRPR | HNRPR protein (Fragment) |
| A0A024R3T8 | PARP1 hCG_14746 | Poly [ADP-ribose] polymerase (PARP) (EC 2.4.2.30) |
| P09874 | PARP1 ADPRT PPOL | Poly [ADP-ribose] polymerase 1 (PARP-1) (EC 2.4.2.30) (ADP-ribosyltransferase diphtheria toxin-like 1) (ARTD1) (NAD(+) ADP-ribosyltransferase 1) (ADPRT 1) (Poly[ADP-ribose] synthase 1) |
| Q8IVF2 | AHNAK2 C14orf78 KIAA2019 | Protein AHNAK2 |
| Q9BQG0 | MYBBP1A P160 | Myb-binding protein 1A |
| A6PVS8 | LRRIQ3 LRRC44 | Leucine-rich repeat and IQ domain-containing protein 3 (Leucine-rich repeat-containing protein 44) |
| A8K6K6 | | cDNA FLJ76880 |
| A8K2G7 | | cDNA FLJ76071, highly similar to *Homo sapiens* filamin A interacting protein 1 (FILIP1), mRNA |
| B0AZQ4 | | Structural maintenance of chromosomes protein |
| Q9P1Z9 | CCDC180 C9orf174 KIAA1529 | Coiled-coil domain-containing protein 180 |
| Q9UFH2 | DNAH17 DNAHL1 DNEL2 | Dynein heavy chain 17, axonemal (Axonemal beta dynein heavy chain 17) (Axonemal dynein heavy chain-like protein 1) (Ciliary dynein heavy chain 17) (Ciliary dynein heavy chain-like protein 1) (Dynein light chain 2, axonemal) |
| B2R5B3 | | Histone H2A |
| B2RAM8 | | cDNA, FLJ95007, highly similar to *Homo sapiens* BRCA1 associated RING domain 1 (BARD1), mRNA |
| Q68CZ1 | RPGRIP1L FTM KIAA1005 NPHP8 | Protein fantom (Nephrocystin-8) (RPGR-interacting protein 1-like protein) (RPGRIP1-like protein) |
| Q2QL34 | MPV17L | Mpv17-like protein (M-LP homolog) (M-LPH) |
| Q13948 | CUX1 CUTL1 | Protein CASP |
| B3KX72 | | cDNA FLJ44920 fis, clone BRAMY3011501, highly similar to Heterogeneous nuclear ribonucleoprotein U |
| Q9NVI7 | ATAD3A | ATPase family AAA domain-containing protein 3A |
| B3KS36 | | cDNA FLJ35376 fis, clone SKMUS2004044, highly similar to *Homo sapiens* ribosomal protein L3 (RPL3), transcript variant 2, mRNA |
| D7EZH4 | | SNF2LT |
| Q9C0G6 | DNAH6 DNAHC6 DNHL1 HL2 KIAA1697 | Dynein heavy chain 6, axonemal (Axonemal beta dynein heavy chain 6) (Ciliary dynein heavy chain 6) |
| O60524 | NEMF SDCCAG1 | Nuclear export mediator factor NEMF (Antigen NY-CO-1) (Serologically defined colon cancer antigen 1) |
| B4DWU6 | | cDNA FLJ51361, highly similar to Keratin, type II cytoskeletal 6A |
| B4DXG0 | | cDNA FLJ57651, highly similar to Ketosamine-3-kinase (EC 2.7.1.—) |
| B4DGN6 | | cDNA FLJ50007 |
| B4DXQ8 | | cDNA FLJ52940, highly similar to Mortality factor 4-like protein 2 |
| Q7L099 | RUFY3 KIAA0871 | Protein RUFY3 (RUN and FYVE domain-containing protein 3) (Rap2-interacting protein x) (RIPx) (Single axon-regulated protein) (Singar) |
| Q9C099 | LRRCC1 CLERC KIAA1764 | Leucine-rich repeat and coiled-coil domain-containing protein 1 (Centrosomal leucine-rich repeat and coiled-coil domain-containing protein) |
| B4DYY8 | | cDNA FLJ60374 |
| Q14439 | GPR176 | G-protein coupled receptor 176 (HB-954) |
| B4DZM3 | | cDNA FLJ61500, highly similar to NNP-1 protein |
| P62318 | SNRPD3 | Small nuclear ribonucleoprotein Sm D3 (Sm-D3) (snRNP core protein D3) |
| B4E1T1 | | cDNA FLJ54081, highly similar to Keratin, type II cytoskeletal 5 |
| B4DLB1 | | cDNA FLJ58017, moderately similar to Treacle protein |
| Q8TC59 | PIWIL2 HILI | Piwi-like protein 2 (EC 3.1.26.—) (Cancer/testis antigen 80) (CT80) |

TABLE 1-continued

Genes encoding proteins that modulate nucleic acid delivery vehicle uptake. The RNAi molecules of the instant disclosure may inhibit expression of one or more of the genes listed in the table.

| Uniprot ID | Gene names | Protein names |
|---|---|---|
| Q16513 | PKN2<br>PRK2<br>PRKCL2 | Serine/threonine-protein kinase N2 (EC 2.7.11.13) (PKN gamma) (Protein kinase C-like 2) (Protein-kinase C-related kinase 2) |
| O75923 | DYSF<br>FER1L1 | Dysferlin (Dystrophy-associated fer-1-like protein) (Fer-1-like protein 1) |
| Q5RF89 | DKFZp469P0721 | Putative uncharacterized protein DKFZp469P0721 |
| Q9UBN4 | TRPC4 | Short transient receptor potential channel 4 (TrpC4) (Trp-related protein 4) (hTrp-4) (hTrp4) |
| P62826 | RAN<br>ARA24<br>OK/SW-cl.81 | GTP-binding nuclear protein Ran (Androgen receptor-associated protein 24) (GTPase Ran) (Ras-like protein TC4) (Ras-related nuclear protein) |
| Q6NTA2 | HNRNPL | HNRNPL protein (Fragment) |
| B4DPC0 | | cDNA FLJ52713, moderately similar to Mus musculus leucine rich repeat (in FLII) interacting protein 1 (Lrrfip1), mRNA |
| B7Z2C5 | | cDNA FLJ50492, highly similar to Cyclin-dependent kinase-like 3 (EC 2.7.11.22) |
| Q86TI0 | TBC1D1<br>KIAA1108 | TBC1 domain family member 1 |
| Q15233 | NONO<br>NRB54 | Non-POU domain-containing octamer-binding protein (NonO protein) (54 kDa nuclear RNA- and DNA-binding protein) (55 kDa nuclear protein) (DNA-binding p52/p100 complex, 52 kDa subunit) (NMT55) (p54(nrb)) (p54nrb) |
| B7Z4E3 | RPL31 | 60S ribosomal protein L31 (cDNA FLJ58908, highly similar to 60S ribosomal protein L31) |
| B7Z7K9 | | CDNA FLJ51382 |
| Q92833 | JARID2<br>JMJ | Protein Jumonji (Jumonji/ARID domain-containing protein 2) |
| Q8N398 | VWA5B2 | von Willebrand factor A domain-containing protein 5B2 |
| Q9BVH8 | VWA5B2 | VWA5B2 protein (Fragment) |
| Q6ZU80 | CEP128<br>C14orf145<br>C14orf61 | Centrosomal protein of 128 kDa (Cep128) |
| P46013 | MKI67 | Proliferation marker protein Ki-67 (Antigen identified by monoclonal antibody Ki-67) (Antigen KI-67) (Antigen Ki67) |
| A2A547 | Rpl19 | Ribosomal protein L19 |
| E4W6B6 | RPL27 | RPL27/NME2 fusion protein (Fragment) |
| O15050 | TRANK1<br>KIAA0342<br>LBA1 | TPR and ankyrin repeat-containing protein 1 (Lupus brain antigen 1 homolog) |
| B3KQL5 | | cDNA FLJ90678 fis, clone PLACE1005736, highly similar to Pleckstrin homology domain-containing family A member 1 |
| Q9HB21 | PLEKHA1<br>TAPP1 | Pleckstrin homology domain-containing family A member 1 (PH domain-containing family A member 1) (Tandem PH domain-containing protein 1) (TAPP-1) |
| O60264 | SMARCA5<br>SNF2H<br>WCRF135 | SWI/SNF-related matrix-associated actin-dependent regulator of chromatin subfamily A member 5 (SWI/SNF-related matrix-associated actin-dependent regulator of chromatin A5) (EC 3.6.4.—) (Sucrose nonfermenting protein 2 homolog) (hSNF2H) |
| Q14789 | GOLGB1 | Golgin subfamily B member 1 (372 kDa Golgi complex-associated protein) (GCP372) (Giantin) (Macrogolgin) |
| A0A087WUK2 | HNRNPDL<br>HNRPDL<br>hCG_22986 | Heterogeneous nuclear ribonucleoprotein D-like (Heterogeneous nuclear ribonucleoprotein D-like, isoform CRA_b) |
| O14979 | HNRNPDL<br>HNRPDL<br>JKTBP | Heterogeneous nuclear ribonucleoprotein D-like (hnRNP D-like) (hnRNP DL) (AU-rich element RNA-binding factor) (JKT41-binding protein) (Protein laAUF1) |

In one aspect, the active agent may be selected from one or more compounds as listed in Table 2.

TABLE 2

Compounds that inhibit proteins that inhibit nucleic acid delivery vehicle uptake.

| Compound name | Structure | Source | CAS registry | Pubchem ID | PMID |
|---|---|---|---|---|---|
| Geldanamycin and derivative Alvespimycin | 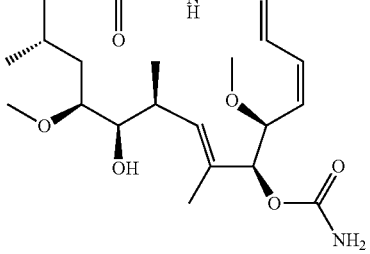 | Multiple, Wutech Acorn PharmaTech Product List ZINC OWNED by, Novartis | 30562-34-6 | 5288382 | 1551101 2656616 |
| Entasobulin | 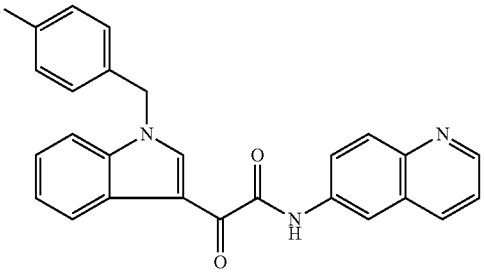 | Multiple, ZINC MedChem express MCE ChemScene | 501921-61-5 | 10203597 | |
| Androstanolone/ Dihydrotestosterone | 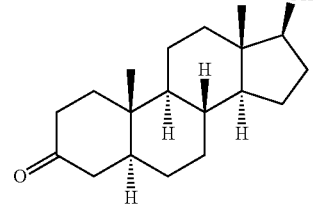 | Multiple, Sigma-Aldrich Key Organics/BIONET 1717 CheMall Corporation OWNED by, | 12040-51-6, 28801-96-9, 29873-50-5, 521-18-6, 571-22-2 | 10635, 15 | 16604538 20035615 20427476 |
| Spermine | 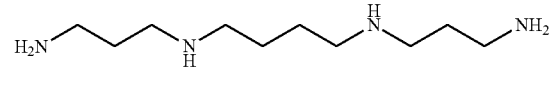 [SMILES: NCCCNCCCCNCCCN] | Multiple, Finetech Industry Limited AK Scientific, Inc. (AKSCI) Sigma-Aldrich | 71-44-3 | 1103 | 26962873 6534776 20427476 3878 |
| Cortisone | 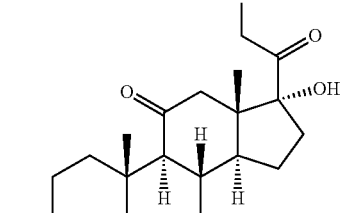 | Multiple, Ambinter LGC Standards AKos Consulting & Solutions | 53-06-5 | 222786 | 24 27856655 |

TABLE 2-continued

Compounds that inhibit proteins that inhibit nucleic acid delivery vehicle uptake.

| Compound name | Structure | Source | CAS registry | Pubchem ID | PMID |
|---|---|---|---|---|---|
| Quercetin | 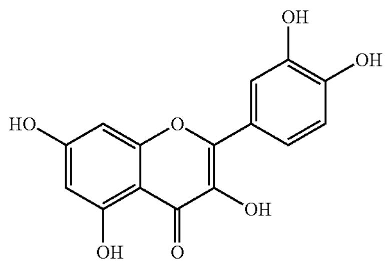 [SMILES: O=c1c(O)c(-c2ccc(O)c(O)c2)oc2cc(O)cc(O)c12] | Multiple, BePharm Ltd. Ambinter TimTec | 117-39-5, 6151-25-3, 7255-55-2, 73123-10-1, 74893-81-5 | 5280343 | 28574574 |
| Acetohexamide | 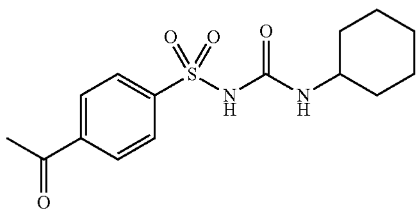 [SMILES: CC(=O)c1ccc(S(=O)(=O)NC(=O)NC2CCCCC2)cc1] | Multiple, TargetMol Boc Sciences Angene Chemical OWNED by, Watson Lilly | 8054-32-8, 968-81-0 | 1989 | 21249 22645689 |
| Resveratrol | 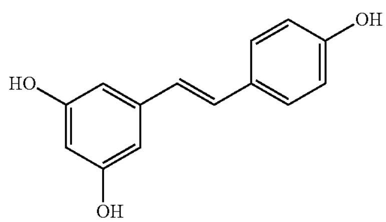 [SMILES: Oc1ccc(/C=C/c2cc(O)cc(O)c2)cc1] | Multiple, 1717 CheMall Corporation ApexBio Technology Selleckchem OWNED by, Home Aide Diagnostics, Inc. | 501-36-0 | 445154 | 7497631 28499732 28406974 |
| Doxorubicin | 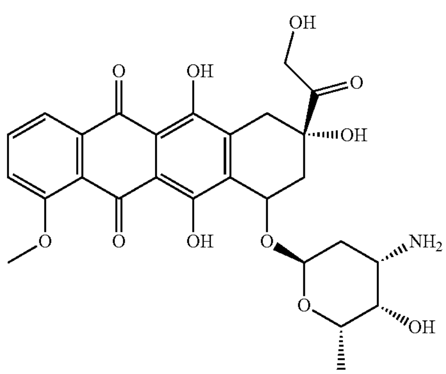 [SMILES: COc1cccc2c1C(=O)c1c(O)c3c(c(O)c1C2=O)C[C@@](O)(C(=O)CO)CC3O[C@H]1C[C@H](N)[C@H](O)[C@H](C)O1] | Multiple, AbovChem LLC Alsachim ABBLIS Chemicals OWNED by, Pfizer | 23214-92-8, 25316-40-9 | 31703 | 3405 14644 28657372 28718370 |
| Ruxolitinib | 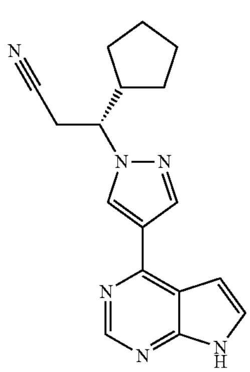 [SMILES: N#CC[C@H](C1CCCC1)n1cc(-c2ncnc3[nH]ccc23)cn1] | Multiple, BePharm Ltd. AvaChem Scientific Active Biopharma OWNED by, Novartis | 1092939-17-7 | 25126798 | 19385672 19468275 28520871 |

TABLE 2-continued

Compounds that inhibit proteins that inhibit nucleic acid delivery vehicle uptake.

| Compound name | Structure | Source | CAS registry | Pubchem ID | PMID |
|---|---|---|---|---|---|
| Roscovitine/ Seliciclib | 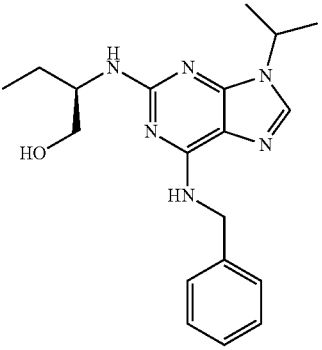 [SMILES: CC[C@H](CO)Nc1nc(NCc2ccccc2)c2ncn(C(C)C)c2n1] | Multiple, Tocris Bioscience abcr GmbH Boc Sciences OWNED by, Cyclacel Pharmaceuticals Inc. | 186692- 44-4 | 5097 | 26962873 9046330 20692737 |
| Sildenafil | 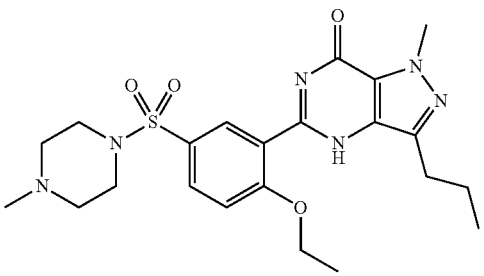 [SMILES: CCCc1nn(C)c2c(=O)nc(-c3cc(S(=O)(=O)N4CCN(C)CC4)ccc3OCC)[nH]c12] | Multiple, OXCHEM CORPORATION MolPort Vitas-M Laboratory OWNED by, Pfizer Actavis Pharma Company | 139755- 83-2, 171599- 83-0 | 5212 | 28652262 28535536 28640077 |
| Teniposide/Vumon | 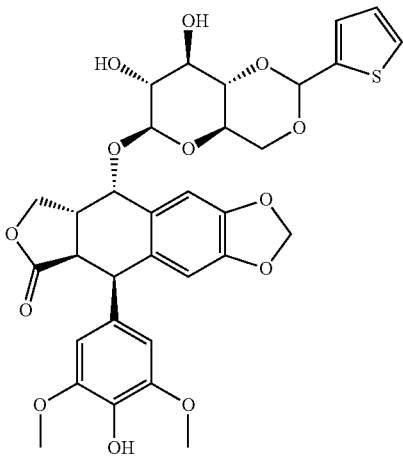 | Multiple, AK Scientific, Inc. AbovChem LLC Boc Sciences OWNED by, WG Critical Care, LLC Bristol Myers Squibb | 23362- 13-2, 29767- 20-2, 31514- 29-1, 35317- 44-3 | 34698 | 26916150 26583611 22771706 |

Description of Agents in Table 2.

Geldanamycin is a benzoquinone ansamycin that binds to the heat shock protein Hsp90 and activates a heat shock response in mammalian cells.

Entasobulin is the first anticancer drug in development involving two mechanisms of action, tubulin and topoisomerase II inhibition. Entasobulin expresses different modes of action such as, pro-apoptotic and anti-angiogenic properties.

Dihydrotestosterone (DHT) (INN: androstanolone) is a biologically active metabolite of the hormone testosterone, formed primarily in the prostate gland, testes, hair follicles, and adrenal glands by the enzyme 5-alpha-reductase by means of reducing the alpha 4, 5 double-bond. Dihydrotestosterone belongs to the class of compounds called androgens, also commonly called androgenic hormones or testoids. DHT is thought to be approximately 30 times more potent than testosterone because of increased affinity to the androgen receptor.

Spermine is a polyamine involved in cellular metabolism found in all eukaryotic cells. The precursor for synthesis of spermine is the amino acid ornithine. It is found in a wide variety of organisms and tissues and is an essential growth factor in some bacteria. It is found as a polycation at physiological pH. Spermine is associated with nucleic acids and is thought to stabilize helical structure, particularly in viruses.

Cortisone is a Corticosteroid. The mechanism of action of cortisone is as a Corticosteroid Hormone Receptor Agonist.

Quercetin is a flavonoid and more specifically a flavonol and represents 60% of the total dietary flavonols intake. The term flavonoid comprises several thousand plant derived compounds sharing a common skeleton of phenyl-chromane. This basic structure allows a multitude of substitution patterns leading to several flavonoid subclasses such as flavonols, flavones, flavanones, catechins, anthocyanidins, isoflavones, dihydroflavonols and chalcones.

The first generation sulfonylureas include acetohexamide, chlorpropamide, tolazamide and tolbutamide, oral hypoglycemic agents that are used in therapy of type 2 diabetes.

Resveratrol (3,5,4'-trihydroxystilbene) is a polyphenolic phytoalexin. It is a stilbenoid, a derivate of stilbene, and is produced in plants with the help of the enzyme stilbene synthase. It exists as two structural isomers: cis-(Z) and trans-(E), with the trans-isomer shown in the top image. The trans-form can undergo isomerization to the cis-form when heated or exposed to ultraviolet irradiation. In a 2004 issue of Science, Dr. Sinclair of Harvard University said resveratrol is not an easy molecule to protect from oxidation. It has been claimed that it is readily degraded by exposure to light, heat, and oxygen. However, studies find that Trans-resveratrol undergoes negligible oxidation in normal atmosphere at room temperature.

Doxorubicin is a drug used in cancer chemotherapy. It is an anthracycline antibiotic, closely related to the natural product daunomycin, and like all anthracyclines it intercalates DNA. It is commonly used in the treatment of a wide range of cancers, including hematological malignancies, many types of carcinoma, and soft tissue sarcomas. The drug is administered in the form of hydrochloride salt intravenously. It may be sold under the brand names Adriamycin PFS, Adriamycin RDF, or Rubex. It is photosensitive and it is often covered by an aluminum bag to prevent light from affecting it.

Ruxolitinib (INCB018424) is a selective oral JAK1/JAK2 inhibitor. This agent has the potential to modulate two important kinases that may play a role in myeloproliferative neoplasms, including primary myelofibrosis.

Roscovitine is a Potent and Selective Inhibitor of the Cyclin-Dependent Kinases cdc2, cdk2 and cdk5.

Sildenafil is a selective PDE5 inhibitor that is used to treat erectile dysfunction and pulmonary arterial hypertension.

Teniposide/Vumon is a semisynthetic derivative of podophyllotoxin with antineoplastic activity. Teniposide forms a ternary complex with the enzyme topoisomerase II and DNA, resulting in dose-dependent single- and double-stranded breaks in DNA, DNA: protein cross-links, inhibition of DNA strand religation, and cytotoxicity. This agent acts in the late S or early G phase of the cell cycle.

TABLE 3

Compounds that inhibit proteins that inhibit nucleic acid delivery vehicle uptake

| # | Drug | Gene Symbol | Target | Effect | Pubmed |
|---|---|---|---|---|---|
| 1 | Entasobulin intracellular | TOP2B | TOP2 beta | Inhibition | |
| 2 | Memantine extracellular region | GRIN3A | NR3A | Inhibition | 17157509 |
| 3 | Teniposide intracellular | TOP2B | TOP2 beta | Inhibition | 8967966 |
| 4 | Etoposide intracellular | TOP2B | TOP2 beta | Inhibition | 1312600, 1312601, 1662724, 2158562, 2167985, 2537424, 2550587, 2849640, 7473578, 7922123, 8120864, 8295216, 8410993, 9211397, 10395485, 10809021, 11754608, 12877556, 15008514, 15084135, 15158802, 15177438, 16242334, 16903072, 17035025, 17580961, 14504921 |
| 5 | INO 1001 intracellular | PARP1 | PARP-1 | Inhibition | 15523000, 18535785, 20364863, 14523042 |
| 6 | Diazoxide intracellular | ABCC8 | SUR1 | Activation | 10419549, 11073882, 11121575, 12023875, 12565699, 14741296, 15561900 |
| 7 | Tedisamil extracellular region | ABCC8 | SUR1 | Inhibition | 10445672, 10684468, 10829253 |
| 8 | Glimepiride intracellular | ABCC8 | SUR1 | Inhibition | 9779817, 10773014, 11078468, 12819907, 20055691, 11325810 |
| 9 | Epirubicin intracellular | TOP2B | TOP2 beta | Inhibition | 16322310 |
| 10 | Annamycin intracellular | TOP2B | TOP2 beta | Inhibition | 15542779 |
| 11 | As(,2)O(,3) intracellular | PARP1 | PARP-1 | Inhibition | 12883267 |
| 12 | (R/S)-Repaglinide extracellular region | ABCC8 | SUR1 | Inhibition | 10773014, 11440368, 11716850, 12196472, 12623163, 12819907, 15200348, 15219283, 15380228, 15678092 |

TABLE 3-continued

Compounds that inhibit proteins that inhibit nucleic acid delivery vehicle uptake

| # | Drug | Gene Symbol | Target | Effect | Pubmed |
|---|---|---|---|---|---|
| 13 | TOP53 intracellular | TOP2B | TOP2 beta | Inhibition | 11170388 |
| 14 | Acetohexamide extracellular region | ABCC8 | SUR1 | Activation | 15200348, 15561903 |
| 15 | Elsamitrucin intracellular | TOP2B | TOP2 beta | Inhibition | 8280493 |
| 16 | Ketamine extracellular region | GRIN3A | NR3A | Inhibition | 17084865, 8336337, 8941398, 9719604, 11937336 |
| 17 | NK109 intracellular | TOP2B | TOP2 beta | Inhibition | 9303354 |
| 18 | Tifenazoxide extracellular region | ABCC8 | SUR1 | Activation | 12213059, 12961066, 14514634, 14764798, 15220194 |
| 19 | Olaparib intracellular | PARP1 | PARP-1 | Inhibition | 18800822, 22343925, 23049934 |
| 20 | Intoplicine intracellular | TOP2B | TOP2 beta | Inhibition | 8043587 |

The gene transfer may occur in the context of administration to a cell in a human, i.e., administration of a vector containing a nucleic acid to a mammal, particularly a human. For example, an individual may be administered a compound and/or RNAi as disclosed herein prior to administration of a nucleic acid delivery system as known in the art (exemplary nucleic acid delivery systems are known in the art and disclosed in References 11-16). The nucleic acid may be single stranded or double stranded, or may, in certain instances, utilize multiple delivery vehicles which may employ one or the other or both.

The nanoparticle delivery vehicle may take a variety of forms. For example, in one aspect, the nucleic acid delivery vehicle may be a nanoparticle comprising said gene. In one aspect, the nucleic acid delivery vehicle may be a nanoparticle comprising a lysine polymer conjugated to PEG and complexed with a nucleic acid comprising the gene.

In one aspect, the proteins that inhibit the nucleic acid delivery vehicle uptake may be selected from keratin 13, APC protein, protocadherin 17, spectrin alph (non-erythrocytic 1), or a combination thereof.

In one aspect, a period of time exists between step a and step b. In aspects in which the nucleic acid delivery vehicle is administered following delivery of an RNAi and/or compound as disclosed herein, the nucleic acid delivery vehicle may be administered to an individual in need thereof, for example, 30 minutes, or 60 minutes, or 90 minutes, or 120 minutes following the administration of a compound and/or RNAi as disclosed herein. In the case of RNAi, in some aspects, the RNAi may be administered about 12 hours in advance of a nucleic acid delivery vehicle, about 20 hours in advance of a nucleic acid delivery vehicle, about 24 hours in advance of a nucleic acid delivery vehicle, or about 30 hours in advance of administration of the delivery vehicle.

For example, for RNAi application, patient stem cells or patient derived iPSCs are harvested and cultured and treated with RNAi against a gene in Table 1 for 24 hr. NNPs formulated to contain an expression cassette for the therapeutic gene are then added to the cells for 72 hr. Reagents and delivery vector are replaced daily. An example of the time involved for the active agent application method is; patients are treated with one or more of the compounds claimed Tables 2 and 3 about 30 to about 60 minutes prior to gene delivery vector administration. Agent treatment may be conducted one or more times before gene therapy. NNPs containing an expression cassette for the therapeutic gene may then be administered to the airways of the patient, for example, via nebulization.

In one aspect, the method may include the step of providing a reagent that facilitates transfection. In one aspect, said agent may be a cationic lipid transfection reagent (e.g. Lipofectamine or GL67), which may be mixed with a nucleic acid under a given formulation to produce a nucleic acid/lipid complex. For lipid (or protein) nucleic acid complexes, any formulation that produces lipid/nucleic acid or protein/nucleic acid complexes (of which there are 1000s) can be combined with the methods herein. This may similarly apply to protein polymers such PEGylated poly L lysine or PEI. For viral vectors, the vector may be produced in cell lines, purified and used for therapy in accordance with the disclosed methods.

Compositions comprising RNAi and/or the compounds of Tables 2 and/or 3 may be administered intranasally. In such aspect, the compositions may further comprise other agents suited for improved delivery across nasal mucosa. For example, in certain aspects, agents such as a permeation enhancer, a polymer capable of increasing mucosal adhesion of the composition, or a combination thereof may be included in the composition.

It will be appreciated by those skilled in the art that the particular method of administration will depend on a variety of factors, all of which are considered routinely when administering therapeutics, particularly in the context of gene transfer. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses o given for a defined number of days, can be ascertained by those skilled in the art using conventional treatment tests.

Kits

Kits are also provided. In one aspect, a kit may comprise or consist essentially of agents or compositions described herein. The kit may be a package that houses a container which may contain one or more compounds or solutions containing an RNAi as disclosed herein, and also houses instructions for administering the agent or composition to a subject. In one aspect, a pharmaceutical pack or kit is provided comprising one or more containers filled with one or more composition as disclosed herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration.

As there may be advantages to mixing a component of a composition described herein and a pharmaceutically acceptable carrier, excipient or vehicle near the time of use, kits in which components of the compositions are packaged separately are disclosed. For example, the kit can contain an active ingredient in a powdered or other dry form in, for example, a sterile vial or ampule and, in a separate container within the kit, a carrier, excipient, or vehicle, or a component of a carrier, excipient, or vehicle (in liquid or dry form). In one aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that is diluted prior to administration. Any of the components described herein, any of the carriers, excipients or vehicles described herein, and any combination of components and carriers, excipients or vehicles can be included in a kit.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing (e.g., tubing to facilitate intravenous administration) alcohol swabs and/or the Band-Aid® applicator). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other embodiments, the kits can include pre-mixed compositions and instructions for solubilizing any precipitate that may have formed during shipping or storage. Kits containing solutions of one or more of the aforementioned active agents, or pharmaceutically acceptable salts thereof, and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

EXAMPLES

Method for Enhancing Nucleic Acid Transfer

Applicant has discovered methods for enhancing the efficiency of gene transfer through the use of interference RNA (RNAi) technology or pharmacological agents that modulate the interactome (FIG. 1) of nucleic acid nanoparticles consisting of polymers of lysine conjugated to PEG and complexed with nucleic acids. Both of these approaches have been reduced to practice and achieve significantly higher levels of gene transfer in the context of condensed DNA nanoparticle vectors, resulting in as much as 50-fold greater gene transfer efficiency. These technologies represent a significant enhancement to gene transfer technologies.

By using a novel immunocapture procedure (FIG. 2), Applicant identified protein interactors of polyethylene glycol conjugated DNA nanoparticles. This investigation revealed 474 unique proteins that interact with the nanoparticles as listed in Table 3. Many of these proteins represent a nanoparticle specific transfection interactome, but a number of proteins such as Prohibitin 1 and 2 are also involved in viral as well as liposomal gene delivery. Some of these protein interactors may be inhibiting the cellular uptake of DNA nanoparticles as well as other vectors for the delivery of nucleic acids. The interactome segregated into sites in the cell where nucleic acid particles are delivered (Table 4). In this method, Applicant used RNAi and/or pharmacological agents to modulate the particle interactome and enhance nucleic acid delivery to the nucleus (DNA) or the ribosome (RNA).

TABLE 4

Characteristics of the nucleic acid nanoparticle cellular protein interactome

| Rank | Cellular Processes | Class | Cellular Localization | P Value | False Discovery Rate | Percent of Dataset (%) |
|---|---|---|---|---|---|---|
| 1 | Intermediate filaments | Cytoskeleton | Cytosol | 1.99E−14 | 8.68E−13 | 21.75 |
| 2 | Translation initiation | Translation | Ribosome | 1.05E−16 | 1.37E−14 | 15.45 |
| 3 | Elongation-Termination | Translation | Ribosome | 1.99E−15 | 1.30E−13 | 12.47 |
| 4 | Actin filaments | Cytoskeleton | Cytosol | 4.84E−08 | 1.58E−06 | 10.01 |
| 5 | Chromatin modification | Transcription | Nucleus | 7.80E−06 | 2.04E−04 | 9.71 |
| 6 | Spindle microtubules | Cytoskeleton | Cytosol | 7.16E−04 | 8.53E−03 | 8.08 |

TABLE 4-continued

Characteristics of the nucleic acid nanoparticle cellular protein interactome

| Rank | Cellular Processes | Class | Cellular Localization | P Value | False Discovery Rate | Percent of Dataset (%) |
|---|---|---|---|---|---|---|
| 7 | mRNA processing | Transcription | Nucleus | 1.06E−04 | 1.83E−03 | 7.71 |
| 8 | Cell junctions | Cell adhesion | Cell membrane | 1.21E−04 | 1.83E−03 | 7.61 |
| 9 | Regulation of cytoskeleton rearrangement | Cytoskeleton | Cytosol | 1.25E−04 | 1.83E−03 | 7.22 |

Figure 3:
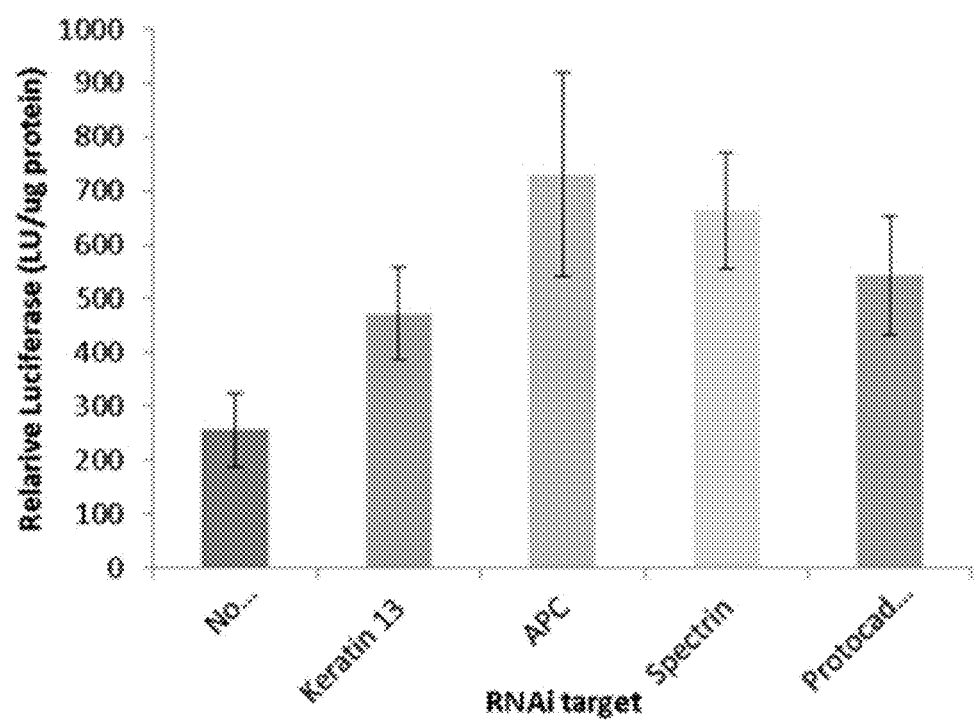
FIG. 3 depicts enhanced DNA nanoparticle transfection through siRNA expression.

For RNAi application, RNAi molecules may be delivered to the cells, or in the case of delivery to an individual, to the individual, prior to the desired nucleic acid delivery vehicle. The RNAi molecules are administered in an amount sufficient to target and knock down specific cellular proteins that negatively impact the uptake of the nucleic acid delivery vehicle. RNAi decreases the cellular levels of these proteins, reducing their deleterious impact on the downstream transfer of nucleic acids. RNAi mediated knockdown of four of these proteins has been tested by Applicant, which resulted in significant enhancement of gene transfer in ¾ constructs tested. RNAi targeted to interfere with the synthesis of the 4 proteins; keratin 13 (GI: 81891678), APC protein (GI: 97535708), protocadherin 17 (GI:94538350), and spectrin alpha (non-erythrocytic 1, GI:119608216) that are deleterious to gene transfer with the DNA nanoparticles improved gene delivery (FIG. 3).

Figure 4:
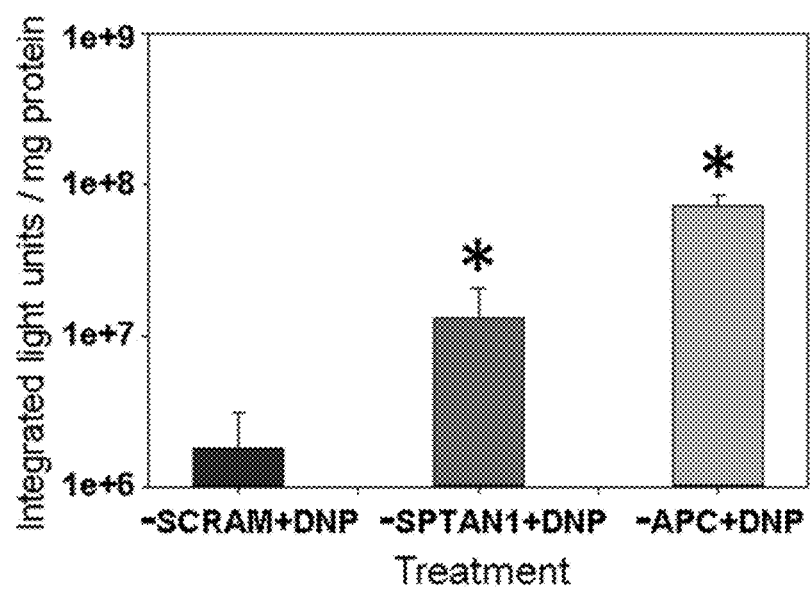
FIG. 4 depicts transfection of human primary airway epithelia either following prior treatment with scrambled shRNA, shRNA specific for APC, or shRNA specific for SPTAN1 for 48 hours. Luciferase expression was measured two days post transfection. * connotes different from saline pretreatment (triplicates in three experiments p<0.01).
Figure 5:
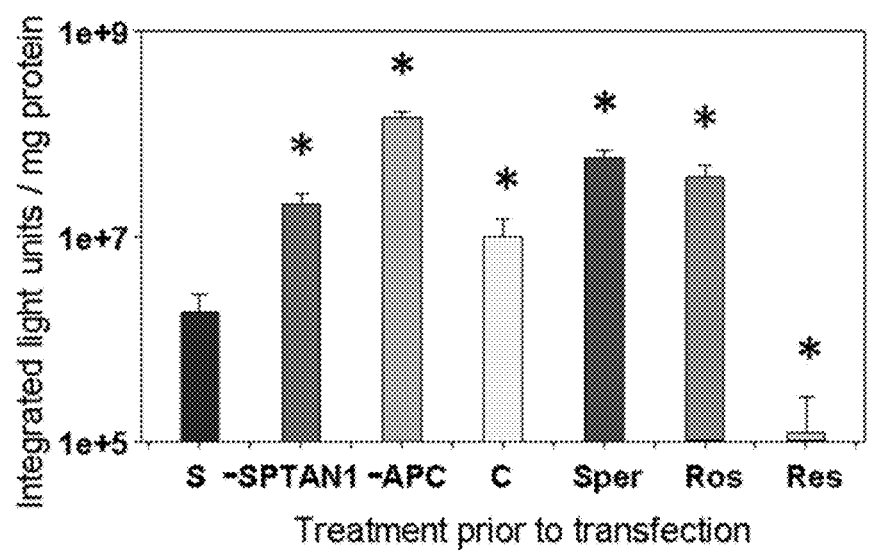
FIG. 5 depicts primary cell cultures of airway epithelia transfected with DNPs containing a plasmid coding for luciferase driven by the ubiquitin B promoter (5.4 kb). shRNA lentivirus infection was 48 hours prior to transfection while spermine (CK11 inducer) roscovitine (CDK1 inhibitor), resveratrol (CDK1 agonist), or cortisone (GR agonist) were added four hours prior to transfection. Treatments were saline (S), APC shRNA (-APC), SPTAN1 shRNA (-SPTAN1), Hydrocortisone©, spermine (Sper), roscovitine (Ros), or resveratrol (RES). Luciferase expression was measured two days post transfection. * connotes different from saline (p<0.01).

In addition or separately, pharmacological agents that modulate the DNP interactome can enhance nucleic acid transfer to the nucleus or the ribosome (in the case of RNA delivery). Applicant found 13 compounds and their derivatives that modulate 71 interactors (see Table 2) that can be administered to patients about 30 to about 60 minutes prior to dosing with DNPs. These are classified by cellular site of action. For example, Doxorubicin and Sildenafil will act to inhibit or promote interactions in the cytosol. Androstanolone will modulate interactions at the ribosome. Acetohexamide will promote non-nucleolin mediated interactions at the cell membrane. Ruxolitinib and Teniposide may be used to modulate nuclear interactions. Applicant's data also points to the importance to the interaction with nucleolin and how modulation of this interaction at the plasma membrane greatly impacts gene transfer with DNPs (FIGS. 3-5). Modulation of these cellular interactions is expected to have different impacts on RNPs vs. DNPs, as the cellular compartment targets for these formulations of NNPs vary (ribosome vs. nucleus, respectively). For example, drugs that promote cellular entry may benefit both DNPs and RNPs. However, drugs that diminish interactions at the ribosome would be expected to only benefit DNPs. Conversely, drugs that diminish nuclear interactions should benefit RNPs.

Table 2 and 3 outlines compounds may be used to modulate nucleolin associated nucleic acid nanoparticle (NNP) uptake. Nucleolin translocation to the cell surface may be promoted by IP injections of roscovitine (inhibits CDK1 at 10 mg/kg), spermine (induces CKII at 50 mg/kg), geldanamycin (inhibits HSP90 interaction with nucleolin at 15 mg/kg), or hydrocortisone (increases GR shuttling of nucleolin to the cell surface at 7.5 mg/kg) into animals 60 min prior to a 25 µl intranasal (IN) administration of 5 µg (with respect to DNA) NNPs containing the CFTR gene, as has been previously reported (1). Control groups injected with either DMSO instead of pharmacological agents, and NNPs containing the transgene with no drug may be used. CF mice may receive NPD measurements 1 week before treatment (a background/baseline measurement) and then 4, 7, and 14 days after transfection with CFTR-containing NNPs applied to the nose, as previously reported (1). Two weeks following transfection mice will be sacrificed, and the lungs may be harvested, paraffin imbeded, and sectioned for immunohistochemistry, and sections probed with the CF3 or 24:1 anti-CFTR Ab that does not cross react with mouse cftr, as previously reported (1). Studies can be duplicated in F508del and S489X homozygote mice.

Use in Research

The RNAi and/or pharmacological approaches to enhancing gene transfer may be developed as an additive to current gene transfer and transfection vectors. For example, it may be used as a supplemental additive to the cationic lipid transfection reagent Lipofectamine, enabling either greater gene transfer or decreased amounts of transfection reagent used, resulting in either reduced costs or enhanced efficiency. Alternatively, pharmacological and RNAi treatment may be employed prior to or concurrent with the delivery of viral vectors in in vitro or ex vivo gene transfer applications. This may allow more cellular gene modification and higher expression of therapeutic transgenes within these cells, or decreased viral titer needed to provide curative levels of cell modification. This may increase the efficacy of these genes or reduce the associated costs with producing sufficient amount of virus, which is currently a significant obstacle in gene therapy protocols.

Use in Human Therapy

Figure 2:
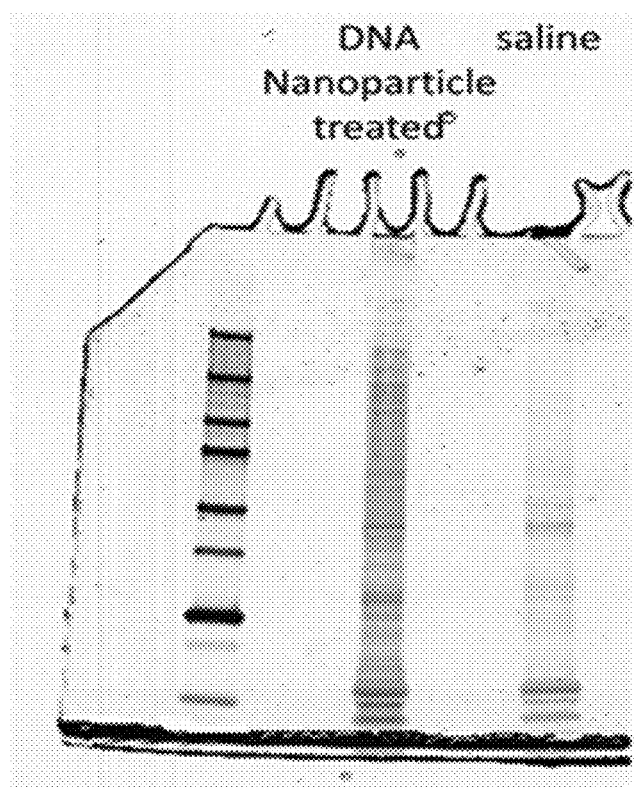
FIG. 2 depicts immunoprecipitation of protein interactors of DNA nanoparticles in HeLa cells.

CF is the most common inherited recessive disorders in Caucasians, and advances in small molecule therapy have not significantly benefitted a large majority of the patients. Gene therapy (repair or replacement) offers a potential of corrective therapy for the disease regardless of mutation type. The disclosed methods may be useful for enhancing corrective DNA and/or RNA delivery with a synthetic vector to airway epithelial cells, the most affected cells in CF. The present example relates to the biology of NNPs, a vector that has been shown to have partial efficacy in correcting CFTR in CF patients (2). Applicant has found 71 specific protein interactors (for example, some of the interactors and associated regulation are shown in FIG. 2, others are listed in Table 1) that help define the biology of the particles in cells and can be targeted with 13 FDA approved drugs (Table 2). Other compounds are listed in Table 3.

Applicant has demonstrated that modulating the NNP interactome can enhance gene transfer by 10-50 fold, the highest levels of enhancement ever achieved in two decades of modifying and examining DNP-based vectors (see FIGS.

3 and 4). Based on this result and given the fact that DNPs have achieved partial clinical correction in a Phase 1 trial in CF patients (2), the methods of the instant disclosure have the potential to provide pharmacological agents that can enhance gene transfer to fully therapeutic levels in humans. While airway epithelial cells are the primary site of disease and the most important gene therapy target in CF, a better understanding of the determinants of successful gene transfer into these cells will significantly benefit gene delivery for a number of other diseases, including chronic obstructive pulmonary disease (COPD; ~12,000,000 patients in the USA), and epithelial lung cancers (~200,000 patients in the USA). The instant disclosure provides a novel approach to implementation of NNP biology. Findings in airway epithelia will likely be relevant to other cell targets where NNPs have succeeded, including cells in the brain (3-6) and retina (7-10), and may be relevant to the cellular uptake of other non-viral polyplex-based vectors as well as viral and liposomal vectors.

In a therapeutic context, siRNA can be applied to human cells ex vivo or pharmacological agents to humans directly before or during gene delivery to optimize gene transfer obtained with DNA/RNA nanoparticles, and potential with liposomal and viral vectors as well.

Example of Application in Cystic Fibrosis

For RNAi application, patient stem cells or patient derived iPSCs are harvested and cultured and treated with RNAi against keratin 13 (GI: 81891678), APC protein (GI: 97535708), protocadherin 17 (GI:94538350), and spectrin alpha (non-erythrocytic 1, GI:119608216) for 24 hr. NNPs formulated to contain an expression cassette for the cystic fibrosis transmembrane conductance regulator (CFTR), the protein mutated in cystic fibrosis, are added to cells for 72 hr. A fraction of cells is tested for CFTR expression, any integration events, and health and morphology, and the remainder of the cells is transferred to the patient.

For pharmacological application, patients may be treated with one or more of the compounds claimed about 30 to about 60 minutes prior to NNP administration. Agent treatment may be conducted once before gene therapy. NNPs contacting an expression cassette for the CFTR gene may be administered to the airways of the patient by nebulization, and gene transfer may be monitored in follow up examinations. The claimed agents may also enhance the delivery of other gene transfer vectors such as liposomal and viral vectors. Pharmacological application may be carried out in combination with RNAi treatment of cells harvested or derived from patients.

REFERENCE LIST

1. Ziady A G, Kelley T J, Milliken E, Ferkol T, Davis P B. Functional evidence of CFTR gene transfer in nasal epithelium of cystic fibrosis mice in vivo following luminal application of DNA complexes targeted to the serpin-enzyme complex receptor. Mol. Ther. 2002 April; 5(4): 413-9
2. Konstan M W, Davis P B, Wagener J S, Hilliard K A, Stern R C, Milgram L J, Kowalczyk T H, Hyatt S L, Fink T L, Gedeon C R, et al. Compacted DNA nanoparticles administered to the nasal mucosa of cystic fibrosis subjects are safe and demonstrate partial to complete cystic fibrosis transmembrane regulator reconstitution. Hum. Gene Ther. 2004 December; 15(12):1255-69
3. Yurek D M, Fletcher A M, Smith G M, Seroogy K B, Ziady A G, Molter J, Kowalczyk T H, Padegimas L, Cooper M J. Long-term transgene expression in the central nervous system using DNA nanoparticles. Mol. Ther. 2009 April; 17(4):641-50
4. Yurek D M, Flectcher A M, Kowalczyk T H, Padegimas L, Cooper M J. Compacted DNA nanoparticle gene transfer of GDNF to the rat striatum enhances the survival of grafted fetal dopamine neurons. Cell Transplant. 2009; 18(10):1183-96. PMCID:PMC3031110
5. Yurek D M, Fletcher A M, McShane M, Kowalczyk T H, Padegimas L, Weatherspoon M R, Kaytor M D, Cooper M J, Ziady A G. DNA Nanoparticles: Detection Of Long-term Transgene Activity In Brain Using Bioluminescence Imaging. Mol. Imaging 2011 Apr. 26;
6. Fletcher A M, Kowalczyk T H, Padegimas L, Cooper M J, Yurek D M. Transgene expression in the striatum following intracerebral injections of DNA nanoparticles encoding for human glial cell line-derived neurotrophic factor. Neuroscience 2011 Oct. 27; 194:220-6. PMCID: PMC3408714
7. Farjo R, Skaggs J, Quiambao A B, Cooper M J, Naash M I. Efficient non-viral ocular gene transfer with compacted DNA nanoparticles. PLoS. One. 2006; 1:e38. PMCID: PMC1762345
8. Ding X Q, Quiambao A B, Fitzgerald J B, Cooper M J, Conley S M, Naash M I. Ocular delivery of compacted DNA-nanoparticles does not elicit toxicity in the mouse retina. PLoS. One. 2009; 4(10):e7410. PMCID: PMC2756629
9. Cai X, Conley S M, Nash Z, Fliesler S J, Cooper M J, Naash M I. Gene delivery to mitotic and postmitotic photoreceptors via compacted DNA nanoparticles results in improved phenotype in a mouse model of retinitis pigmentosa. FASEB J. 2010 April; 24(4):1178-91. PMCID:PMC2845431
10. Koirala A, Makkia R S, Conley S M, Cooper M J, Naash M I. S/MAR-containing DNA nanoparticles promote persistent RPE gene expression and improvement in RPE65-associated LCA. Hum. Mol. Genet. 2013 Apr. 15; 22(8): 1632-42. PMCID:PMC3605833
11. Ziady A G, Davis P B, Konstan M W. Non-viral gene transfer therapy for cystic fibrosis. Expert. Opin. Biol. Ther. 2003 June; 3(3):449-58
12. Ziady A G, Davis P B. Current prospects for gene therapy of cystic fibrosis. Curr. Opin. Pharmacol. 2006 October; 6(5):515-21
13. Ahmed H, Shubina-Oleinik O, Holt J R. Emerging Gene Therapies for Genetic Hearing Loss. J. Assoc. Res. Otolaryngol. 2017 Aug. 16;
14. Naso M F, Tomkowicz B, Perry W L, III, Strohl W R. Adeno-Associated Virus (AAV) as a Vector for Gene Therapy. BioDrugs. 2017 Jul. 1. PMCID:PMC5548848
15. Huang J, Wang Y, Zhao J. CRISPR Editing in Biological and Biomedical Investigation. J. Cell Physiol 2017 Aug. 8;
16. Zhang X, Wang L, Liu M, Li D. CRISPR/Cas9 system: a powerful technology for in vivo and ex vivo gene therapy. Sci. China Life Sci. 2017 May; 60(5):468-75

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for enhancing uptake of a nucleic acid nanoparticle into a eukaryotic cell for administration of a therapeutic gene, comprising
   a. contacting said eukaryotic cell with said nucleic acid nanoparticle (NNP); and
   b. contacting said eukaryotic cell with a nanoparticle uptake enhancing agent selected from one or both of an RNAi molecule and a compound;
   wherein said NNP comprises a nucleic acid encoding said therapeutic gene or active portion thereof, and a cationic polymer conjugated to polyethylene glycol;
   wherein said cationic polymer is selected from a polylysine, a polyethyleneimine, and combinations thereof;
   wherein RNAi molecule inhibits expression of a gene encoding a protein selected from keratin 13, APC protein, protocadherin 17, and spectrin alpha; and
   wherein said compound is selected from geldanamycin, alvespimycin, entasobulin, androstanolone, spermine, cortisone, quercetin, acetohexamide, resveratrol, doxorubicin, ruxolitinib, roscovitine, sildenafil, teniposide, etoposide, 3-Aminobenzamide (INO 1001), diazoxide, tedisamil, glimepiride, epirubicin, annamycin, repaglinide, 4β-aminoalkyl-4'-O-demethyl-4-desoxypodophyllotoxin (TOP53), acetohexamide, elsamitrucin, ketamine, NK109, tifenazoxide, olaparib, intoplicine, and combinations thereof, $As_2O_3$.

2. The method of claim 1, wherein said active agent is selected from roscovitine, geldanamycin, acetohexamide, and ruxolitinib, or a combination thereof.

3. The method of claim 1, wherein said NNP comprises a lysine polymer conjugated to PEG.

4. The method of claim 1, wherein a period of time exists between step a and step b.

5. The method of claim 1, wherein said nucleic acid is single stranded.

6. The method of claim 1, wherein said nucleic acid is double stranded.

7. The method of claim 1, wherein said method is carried out in vitro.

8. The method of claim 1, wherein said method is carried out ex vivo.

9. A method of treating an individual, comprising the step of
   a. administering an RNAi that inhibits expression of one or more genes encoding a protein selected from keratin 13, APC protein, protocadherin 17, spectrin alpha, and combinations thereof, and a compound selected from geldanamycin, alvespimycin, entasobulin, androstanolone, spermine, cortisone, quercetin, acetohexamide, resveratrol, doxorubicin, ruxolitinib, roscovitine, sildenafil, teniposide, etoposide, 3-Aminobenzamide (INO 1001), diazoxide, tedisamil, glimepiride, epirubicin, annamycin, repaglinide, 4β-aminoalkyl-4'-O-demethyl-4-desoxypodophyllotoxin (TOP53), acetohexamide, elsamitrucin, ketamine, NK109, tifenazoxide, olaparib, intoplicine, $As_2O_3$; and
   b. administering a nucleic acid nanoparticle (NNP) comprising a therapeutic gene, or portion of a therapeutic gene that encodes an active portion of a protein, that is expressed in said individual to provide a functional protein or functional protein fragment, wherein said functional protein or functional protein fragment is expressed in said individual in a therapeutically effective amount;
   wherein said NNP comprises a cationic polymer conjugated to polyethylene glycol and;
   wherein said cationic polymer is selected from a poly lysine, a polyethyleneimine, and combinations thereof.

10. The method of claim 9, wherein said one or both of said RNAi and said compound are administered concurrently, before, or after administration of said NNP.

11. The method of claim 1, wherein said NNP comprises a viral vector.

12. The method of claim 1, wherein said NNP comprises a liposomal vector.

13. The method of claim 1, wherein said NNP comprises a lipid complex.

14. The method of claim 1, wherein said NNP comprises nucleic acid components of a CRISPR/CAS9 system.

* * * * *